(12) United States Patent
Zhang et al.

(10) Patent No.: US 10,201,572 B2
(45) Date of Patent: *Feb. 12, 2019

(54) COMBINATION THERAPY WITH DOUBLE NEGATIVE T-CELLS

(71) Applicant: UNIVERSITY HEALTH NETWORK, Toronto (CA)

(72) Inventors: Li Zhang, Toronto (CA); Jong Bok Lee, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/266,756

(22) Filed: Sep. 15, 2016

(65) Prior Publication Data
US 2017/0071983 A1    Mar. 16, 2017

Related U.S. Application Data

(60) Provisional application No. 62/218,925, filed on Sep. 15, 2015.

(51) Int. Cl.
| | | |
|---|---|---|
| A61K 35/17 | (2015.01) | |
| A61K 38/21 | (2006.01) | |
| A61K 9/00 | (2006.01) | |

(52) U.S. Cl.
CPC ............ *A61K 35/17* (2013.01); *A61K 9/0019* (2013.01); *A61K 38/217* (2013.01); *A61K 2300/00* (2013.01)

(58) Field of Classification Search
CPC .............................. A61K 35/17; A61K 38/217
USPC ...................................................... 424/130.1
See application file for complete search history.

(56) References Cited

U.S. PATENT DOCUMENTS

| | | | | |
|---|---|---|---|---|
| 2008/0254045 | A1* | 10/2008 | Donda ................. | A61K 39/385 424/178.1 |
| 2009/0098095 | A1* | 4/2009 | Zhang ................. | C12N 5/0636 424/93.71 |

OTHER PUBLICATIONS

Acquavella et al., "Type I cytokines synergize with oncogene inhibition to induce tumor growth arrest." *Cancer Immunol Res*, 3:37-47, (2015).
Arpinati et al., "Immunotherapy in acute myeloid leukemia." *Immunotherapy*, 6:95-106, (2014).
Bachanova et al., "Clearance of acute myeloid leukemia by haploidentical natural killer cells is improved using IL-2 diphtheria toxin fusion protein." *Blood*, 123:3855-3863, (2014).
Beatty et al., "IFN-γ Can Promote Tumor Evasion of the Immune System In Vivo by Down-Regulating Cellular Levels of an Endogenous Tumor Antigen." *The Journal of Immunology*, 165:5502-5508, (2000).
Bui et al. "IFN-dependent down-regulation of the NKG2D ligand H60 on tumors." *Journal of Immunology*, 176:905-913, (2006).
Campbell et al., "Natural killer cell biology: an update and future direction," *The Journal of Allergy and Clinical Immunology*, 132: 536-544, (2013).
Cerboni et al., "The DNA Damage Response: A Common Pathway in the Regulation of NKG2D and DNAM-1 Ligand Expression in Normal, Infected, and Cancer Cells." *Frontiers in Immunology*, 4:508, (2014).
Cornelissen et al., "The European LeukemiaNet AML Working Party Consensus statement on allogeneic HSCT for patients with AML in remission: an integrated-risk adapted approach," *Nat Rev Clin Oncol*, 9:579-590, (2012).
Covassin et al., "Human peripheral blood CD4 T cell-engrafted non-obese diabetic-scid IL2rgamma(null) H2Ab1 (tm1Gru) Tg (human leucocyte antigen D-related 4) mice: a mouse model of human allogeneic graft-versus-host disease." *Clin Exp Immunol*, 166:269-280, (2011).
Curti et al., "Successful transfer of alloreactive haploidentical KIR ligand-mismatched natural killer cells after infusion in elderly high risk acute myeloid leukemia patients," *Blood*, 118: 3273-3279, (2011).
de Andrade et al., "DNAM-1 control of natural killer cells functions through nectin and nectin-like proteins." *Immunology and Cell Biology*, 92:237-244, (2014).
Drake et al., Human CD34+ CD133+ Hematopoietic Stem Cells Cultured with Growth Factors Including Angptl5 Efficiently Engraft Adult NOD-SCID Il2rγ-/- (NSG) Mice*PLoS One*, 6:e18382, (2011).
Ersvaer et al., "Effects of interferon gamma on native human acute myelogenous leukaemia cells." *Cancer Immunology, immunotherapy: CII*, 56:13-24, (2007).
Farag et al., "Pretreatment cytogenetics add to other prognostic factors predicting complete remission and long-term outcome in patients 60 years of age or older with acute myeloid leukemia: results from Cancer and Leukemia Group B 8461" *Blood* 108: 63-73, (2006).
Fine et al., "Chemotherapy-induced genotoxic stress promotes sensitivity to natural killer cell cytotoxicity by enabling missing-self recognition." *Cancer Res*, 70:7102-7113, (2010).
Fujii et al., "Humanized Chronic Graft-versus-Host Disease in NOD-SCID i12rγ-/- (NSG) Mice with G-CSF-Mobilized Peripheral Blood Mononuclear Cells following Cyclophosphamide and Total Body Irradiation." *PLoS One*, 10:e0133216, (2015).
Gasser et al., "The DNA damage pathway regulates innate immune system ligands of the NKG2D receptor." *Nature*, 436:1186-1190, (2005).
Gertner-Dardenne et al., "Human Vgamma9Vdelta2 T cells specifically recognize and kill acute myeloid leukemic blasts." *Journal of Immunology*, 188: 4701-4708, (2012).
Hoang et al., "Identification of leukemia stem cells in acute myeloid leukemia and their clinical relevance" *Biotechnol J.*, 7: 779-788, (2012).
Hourigan et al., "Minimal residual disease in acute myeloid leukaemia." *Nat Rev Clin Oncol*, 10:460-471, (2013).
June et al., "Adoptive cellular therapy: a race to the finish line," *Sci Transl Med*, 7:280-287, (2015).

(Continued)

*Primary Examiner* — Yan Xiao
(74) *Attorney, Agent, or Firm* — Norton Rose Fulbright US LLP

(57) ABSTRACT

There is provided herein methods of treating leukemia or lymphoma in a subject in need thereof, with double negative T cells (DNTs) in combination with Interferon-γ.

25 Claims, 30 Drawing Sheets

(56) References Cited

OTHER PUBLICATIONS

Karimi et al., "NKG2D expression by CD8+ T cells contributes to GVHD and GVT effects in a murine model of allogeneic HSCT." *Blood*, 125:3655-3663, (2015).
Karp et al., "Randomized phase II study of two schedules of flavopiridol given as timed sequential therapy with cytosine arabinoside and mitoxantrone for adults with newly diagnosed, poor-risk acute myelogenous leukemia," *Haematologica*, 97:1736-1742, (2012).
Majeti et al., "CD47 is an adverse prognostic factor and therapeutic antibody target on human acute myeloid leukemia stem cells." *Cell*, 138:286-299, (2009).
Matsushita et al., "Cytotoxic T lymphocytes block tumor growth both by lytic activity and IFNγ-dependent cell-cycle arrest.." *Cancer Immunol Res*, 3:26-36 (2015).
Maude et al., "Chimeric antigen receptor T cells for sustained remissions in leukemia." *The New England Journal of Medicine*, 371:1507-1517, (2014).
McDermott et al., "Comparison of human cord blood engraftment between immunocompromised mouse strains," *Blood*, 116:193-200, (2010).
Merims et al., "Anti-leukemia effect of ex vivo expanded DNT cells from AML patients: a potential novel autologous T-cell adoptive immunotherapy." *Leukemia*, 25:1415-1422, (2011).
Miller et al., "Successful adoptive transfer and in vivo expansion of human haploidentical NK cells in patients with cancer." *Blood*, 105:3051-3057, (2005).
Montero et al., "T-cell depleted peripheral blood stem cell allotransplantation with T-cell add-back for patients with hematological malignancies: effect of chronic GVHD on outcome," *Biol Blood Marrow Transplant*, 12: 1318-1325, (2006).
Morel et al., "Processing of some antigens by the standard proteasome but not by the immunoproteasome results in poor presentation by dendritic cells." *Immunity*, 12:107-117, (2000).
Nanbakhsh et al., "c-Myc regulates expression of NKG2D ligands ULBP1/2/3 in AML and modulates their susceptibility to NK-mediated lysis." *Blood*, 123:3585-3595, (2014).
Ogbomo et al., "Resistance to cytarabine induces the up-regulation of NKG2D ligands and enhances natural killer cell lysis of leukemic cells." *Neoplasia*, 10:1402-1410, (2008).
Pende et al., "Analysis of the receptor-ligand interactions in the natural killer-mediated lysis of freshly isolated myeloid or lymphoblastic leukemias: evidence for the involvement of the Poliovirus receptor (CD155) and Nectin-2 (CD112)." *Blood*, 105:2066-2073, (2005).
Pizzitola et al., "Chimeric antigen receptors against CD33/CD123 antigens efficiently target primary acute myeloid leukemia cells in vivo." *Leukemia*, 28:1596-1605, (2014).
Rambaldi et al., "Cell-based strategies to manage leukemia relapse: efficacy and feasibility of immunotherapy approaches." *Leukemia*, 29:1-10, (2015).
Raulet, "Roles of the NKG2D immunoreceptor and its ligands." *Nature Reviews Immunology*, 3: 781-790, (2003).
Ritchie et al., "Persistence and efficacy of second generation CAR T cell against the LeY antigen in acute myeloid leukemia." *Mol Ther*, 21:2122-2129, (2013).
Rooney et al., "Can Treg elimination enhance NK cell therapy for AML?" *Blood*, 123:3848-3849. (2014).
Rosenberg et al., "Adoptive cell transfer as personalized immunotherapy for human cancer." *Science*, 348:62-68, (2015).
Ruggeri et al., "Effectiveness of donor natural killer cell alloreactivity in mismatched hematopoietic transplants." *Science*, 295: 2097-2100, (2002).
Sanchez-Correa et al., "Decreased expression of DNAM-1 on NK cells from acute myeloid leukemia patients." *Immunology and Cell Biology*, 90:109-115, (2012).
Schwinn et al., "Interferon-γ down-regulates NKG2D ligand expression and impairs the NKG2D-mediated cytolysis of MHC class I-deficient melanoma by natural killer cells." *International Journal of Cancer. Journal International du Cancer*, 124:1594-1604, (2009).
Shankaran et al., "IFNgamma and lymphocytes prevent primary tumour development and shape tumour immunogenicity." *Nature*, 410:1107-1111, (2001).
She et al., "Resistance of leukemic stem-like cells in AML cell line KG1a to natural killer cell-mediated cytotoxicity," *Cancer letters*, 318: 173-179, (2012).
Soriani et al., "ATM-ATR-dependent up-regulation of DNAM-1 and NKG2D ligands on multiple myeloma cells by therapeutic agents results in enhanced NK-cell susceptibility and is associated with a senescent phenotype." *Blood*, 113:3503-3511, (2009).
Stone et al., "Recombinant human gamma interferon administered by continuous intravenous infusion in acute myelogenous leukemia and myelodysplastic syndromes." *American Journal of Clinical Oncology*, 16:159-163, (1993).
Tettamanti et al., "CD123 AML targeting by chimeric antigen receptors: A novel magic bullet for AML therapeutics?" *Oncoimmunology*, 3:e28835, (2014).
Van den Brink et al., "Relapse after allogeneic hematopoietic cell therapy," *Biol Blood Marrow Transplant*, 16:S138-145, (2010).
van Rijn et al., "A new xenograft model for graft-versus-host disease by intravenous transfer of human peripheral blood mononuclear cells in RAG2–/– gammac–/– double-mutant mice." *Blood*, 102:2522-2531, (2003).
Varela et al., "Interferon-γ Sensitizes Human Myeloid Leukemia Cells to Death Receptor-mediated Apoptosis by a Pleiotropic Mechanism." *The Journal of Biological Chemistry*, 276:17779-17787, (2001).
Verheyden et al., "NK cell receptors and their ligands in leukemia." *Leukemia*, 22:249-257, (2008).
Vincent et al., "Next-generation leukemia immunotherapy," *Blood*, 118: 2951-2959, (2011).
Vyas et al., "Reprint of: Allogeneic hematopoietic cell transplantation for acute myeloid leukemia," *Biol Blood Marrow Transplant*, 21:S3-10, (2015).
Wang et la., "Treatment of CD33-directed chimeric antigen receptor-modified T cells in one patient with relapsed and refractory acute myeloid leukemia." *Mol Ther*, 23:184-191, (2015).
Yanada et al., "Efficacy of allogeneic hematopoietic stem cell transplantation depends on cytogenetic risk for acute myeloid leukemia in first disease remission: a metaanalysis," *Cancer*, 103:1652-1658, (2005).
Young et al., "Antitumor activity mediated by double-negative T cells." *Cancer Res*, 63:8014-8021, (2003).
Zahreddine et al., "The sonic hedgehog factor GLI1 imparts drug resistance through inducible glucuronidation." *Nature*, 511: 90-93 (2014).
Zaidi et al., "The two faces of interferon-γ in cancer." *Clinical Cancer Research*, 17:6118-6124, (2011).
Zhang et al., "NKG2D Ligands in Tumor Immunity: Two Sides of a Coin." *Frontiers in Immunology*, 6:97, (2015).

\* cited by examiner

COMBINATION THERAPY WITH DOUBLE NEGATIVE T-CELLS

CROSS REFERENCE TO RELATED APPLICATIONS

This application claims priority to U.S. Provisional Application No. 62/218,925 filed Sep. 15, 2015, the entire contents of which is specifically incorporated herein by reference without disclaimer.

FIELD OF THE INVENTION

The invention relates to double negative T-Cells (DNTs), and more particularly to their use in cancer therapy along with Interferon-γ.

BACKGROUND OF THE INVENTION

Acute myeloid leukemia (AML) is the most common form of adult acute leukemia with 5 year survival rates of ~5% and ~30% for elder and younger patients, respectively[1-5]. Although >70% of AML patients achieve an initial remission with induction chemotherapy, chemotherapy-resistant leukemia cells ultimately cause relapse in most patients[3,4,6]. Allogeneic hematopoietic stem cell transplantation (allo-HSCT) is a potentially curative treatment for chemotherapy-resistant AML[7-9]. However, transplantation has toxicities restricting its use in older and debilitated patients. Moreover, although allogeneic immune cells can kill leukemic cells[10-14], they commonly also recognize allo-antigens expressed on normal cells and tissues inducing severe, and sometimes lethal graft-versus-host-disease (GvHD)[14-16]. In addition, limited donor availability prevents wide use of allo-HSCT. Hence, development of safer and more effective cell-based therapies for AML is needed.

Double negative T cells (DNTs) are mature peripheral lymphocytes that express the CD3-T cell receptor (TCR) complex, including both αβ- and γδ-TCR, but do not express CD4 and CD8, and are not iNKT cells (FIG. 1b). DNTs represent 1-3% of peripheral blood mononuclear cells (PBMCs)[17]. Previously, we have shown that mouse DNTs could rescue mice from a lethal dose of lymphoma cells and DNTs expanded from AML patients were cytotoxic to autologous AML cells in vitro[17,18]. While we showed that DNTs expressing αβ- and γδ-TCR have comparable level of cytotoxicity[17], the mechanisms by which DNTs mediate their anti-leukemia activity remain unclear and no data exists regarding the in vivo anti-leukemic potential of these immune effectors. Further, it remains unknown whether DNTs expanded from healthy donors (HDs) can target AML cells while sparing non-malignant hematological cells of the donor from which they were derived.

SUMMARY OF THE INVENTION

Here we show that allogeneic DNTs can target a large array of primary AML cells, including those from chemotherapy-resistant AML patients, with no toxicity against normal cells. Furthermore, we have identified molecules involved in DNT-mediated cytotoxicity.

In an aspect, there is provided a method of treating leukemia or lymphoma in a subject in need thereof, comprising administering to the subject an effective amount of double negative T cells (DNTs) and Interferon-γ.

In one aspect, the Interferon-γ is administered to a subject prior to treatment with double negative T cells (DNTs). In yet another aspect the Interferon-γ is administered to a subject immediately prior to treatment with double negative T cells (DNTs).

In an aspect, there is provided a method of treating leukemia or lymphoma in a subject in need thereof, comprising administering to the subject an effective amount of double negative T cells (DNTs), wherein the subject has previously been administered Interferon-γ.

In an aspect, there is provided a method of sensitizing a subject to the treatment of leukemia or lymphoma with double negative T cells (DNTs), comprising administering to the subject an effective amount of Interferon-γ.

In an aspect, there is provided a method of sensitizing leukemic or lymphoma cells to double negative T cells (DNTs) therapy, comprising exposing the cells to Interferon-γ.

In an aspect, there is provided a method of inhibiting the growth or proliferation of leukemia or lymphoma comprising exposing the leukemic or lymphoma cells to double negative T cells (DNTs) and Interferon-γ.

In an aspect, there is provided a use of an effective amount of double negative T cells (DNTs) and Interferon-γ for treating leukemia or lymphoma in a subject in need thereof.

In an aspect, there is provided a use of an effective amount of double negative T cells (DNTs) for treating leukemia or lymphoma in a subject in need thereof and that has been administered Interferon-γ.

In an aspect, there is provided a use of an effective amount of Interferon-γ for sensitizing a subject to the treatment of leukemia or lymphoma with double negative T cells (DNTs).

In an aspect, there is provided a use of an effective amount of double negative T cells (DNTs) and Interferon-γ for inhibiting the growth or proliferation of leukemic or lymphoma cells.

In an aspect, there is provided a use of an effective amount of Interferon-γ for sensitizing leukemic or lymphoma cells to double negative T cells (DNTs) therapy.

In an aspect, there is provided a use of Interferon-γ in the preparation of a medicament for the combination treatment of leukemic or lymphoma cells with double negative T cells (DNTs).

In an aspect, there is provided a pharmaceutical composition comprising double negative T cells (DNTs) and Interferon-γ.

BRIEF DESCRIPTION OF FIGURES

These and other features of the preferred embodiments of the invention will become more apparent in the following detailed description in which reference is made to the appended drawings wherein.

Figure 3:
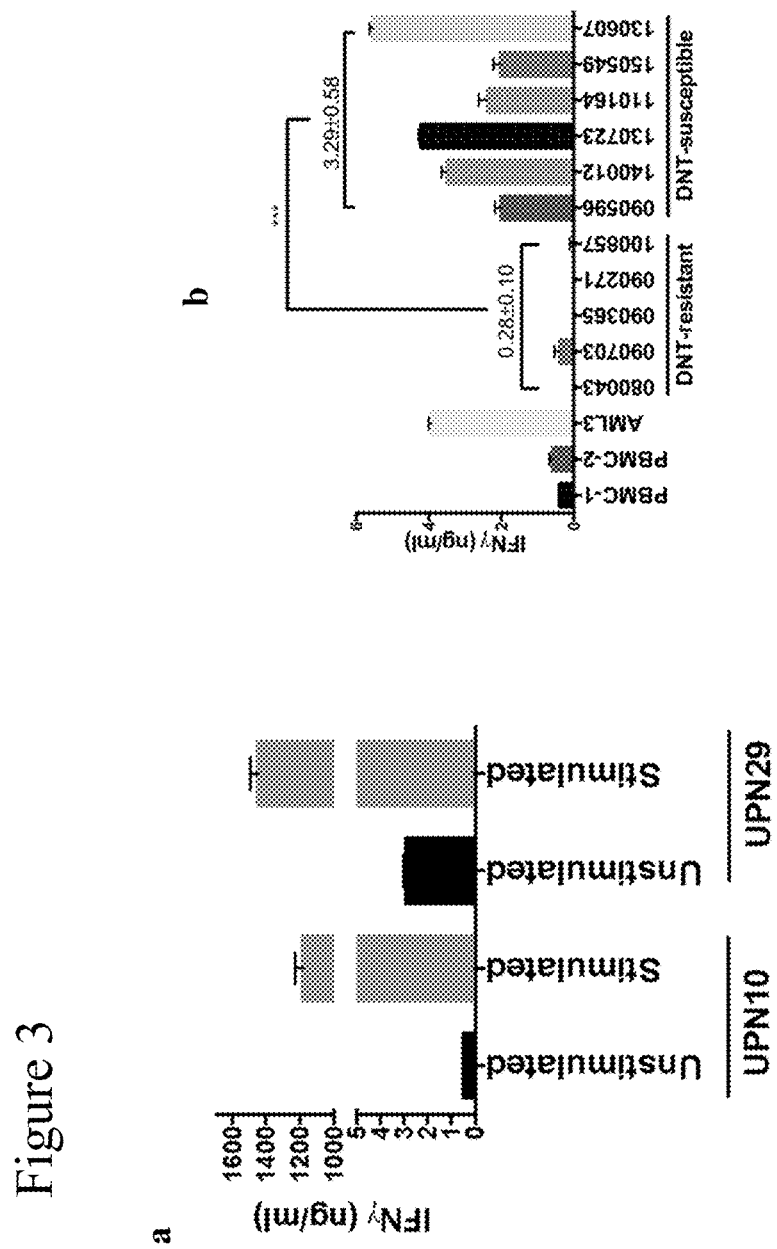
FIG. 3 shows DNTs release IFNγ upon recognizing susceptible AML cells, and exogenous IFNγ increases the level of cytotoxicity by sensitizing the AML targets. (a) IFNγ release by DNTs from two HDs (UPN10 and UPN29) after overnight culture in the presence or absence of PMA-Ionomycin (5 ng/ml) was quantified by ELISA. (b and c) Ex vivo expanded DNTs were co-incubated with allogeneic PBMCs, AML3/OCI, DNT-resistant (n=5), or DNT-susceptible (n=6) primary AML samples at 4:1 effector-to-target ratio for 2 hours, and the level of IFNγ in the culture supernatants was determined by ELISA. The number represents the average amount ±SEM of IFNγ produced from co-cultures of DNT and DNT-resistant or -susceptible primary AML blasts. The data are representative of 3 independent experiments. (d) Ex vivo expanded DNTs were pre-treated with anti-IFNγ antibody for 1 hour before co-incubation with OCI/AML3 or primary blast 080009. DNTs pre-treated with IgG2a isotype control antibody were used as controls. % inhibition of killing was calculated by $$\left(\frac{\%\text{ specific killing}_{No\ Ab} - \%\text{ specific killing}_{with\ Ab}}{\%\text{ specific killing}_{No\ Ab}}\right) \times 100.$$
Figure 3:
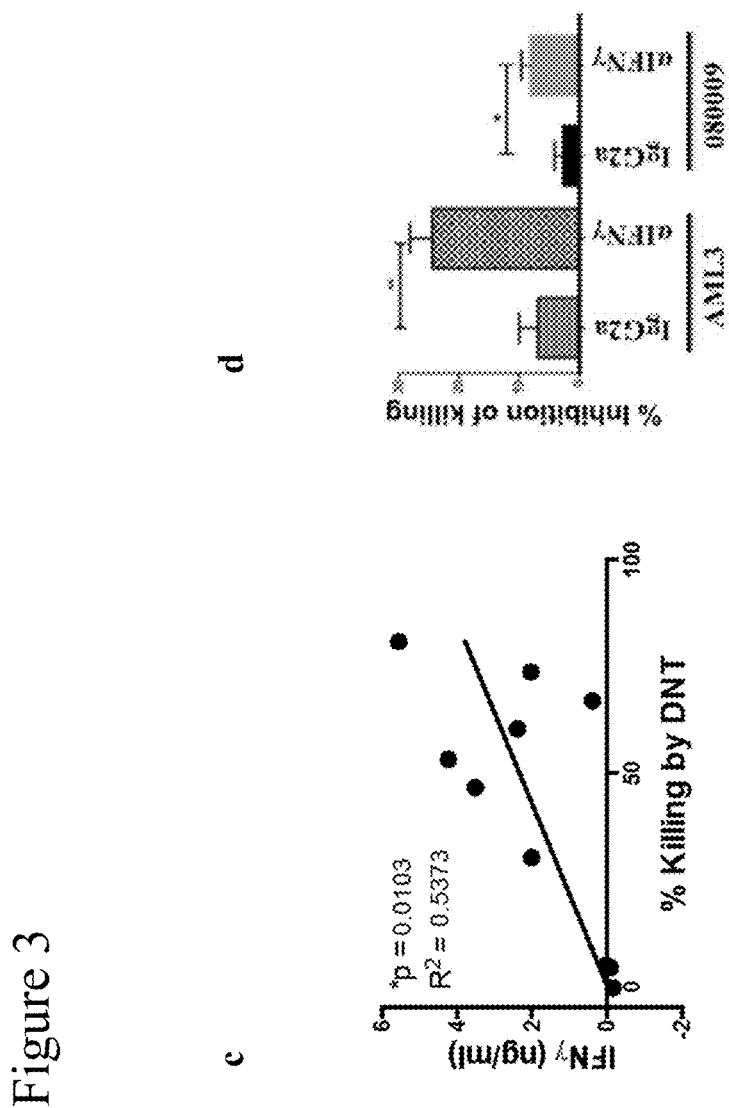
Figure 3:
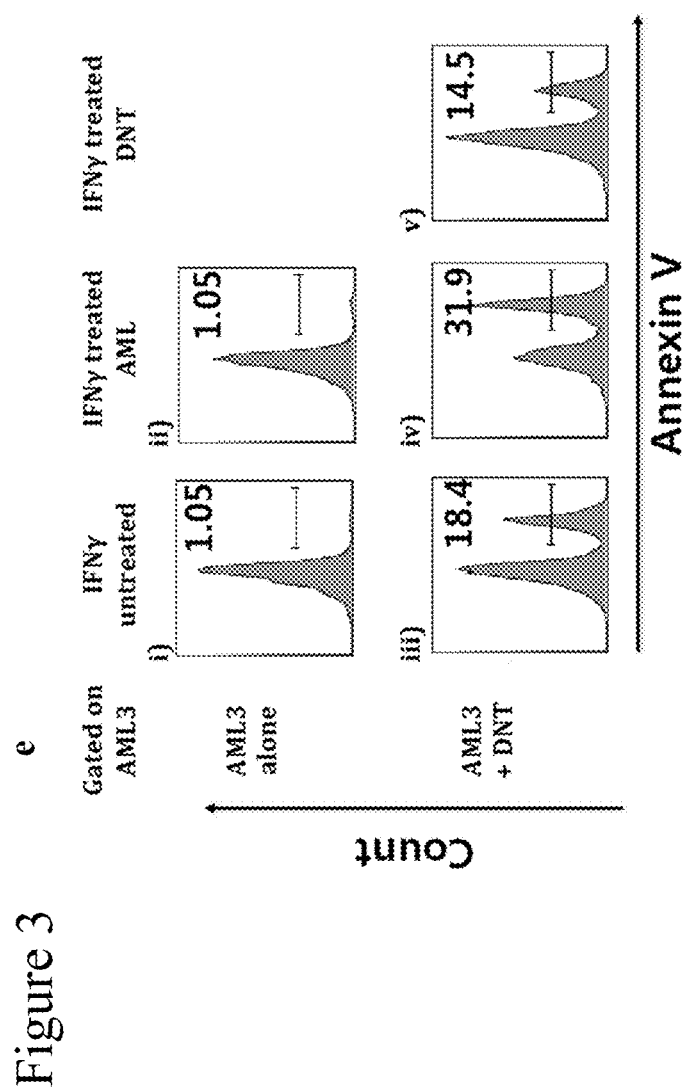
Figure 3:
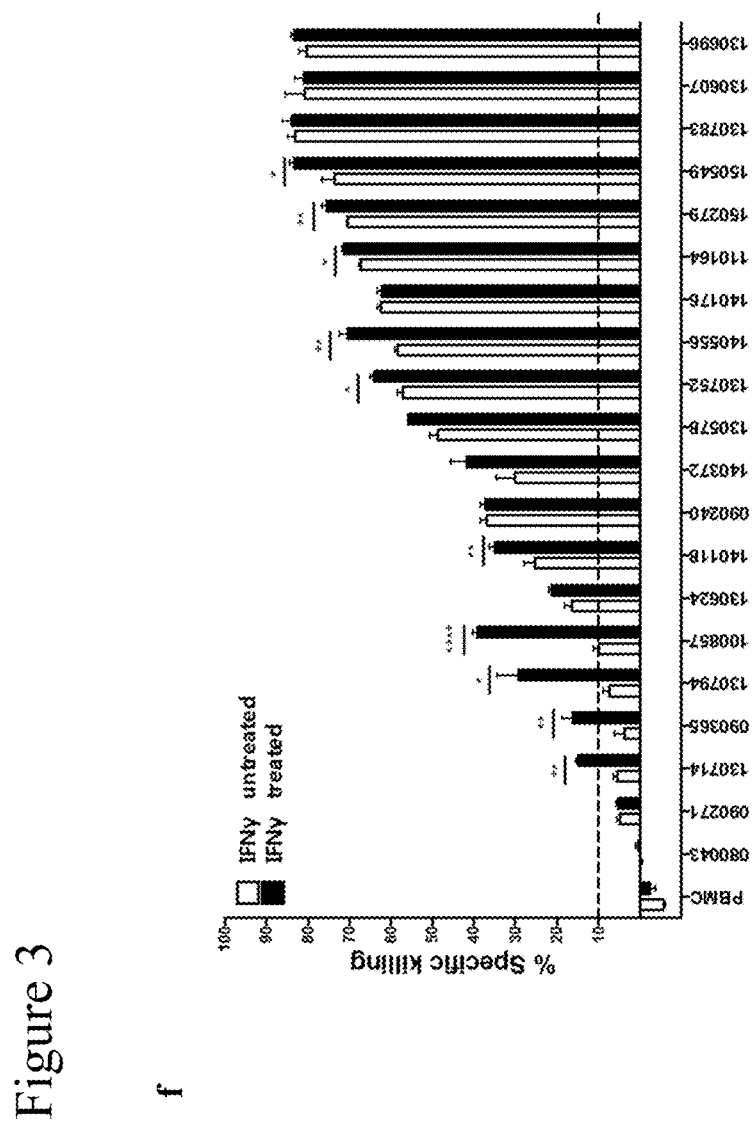
Figure 3:
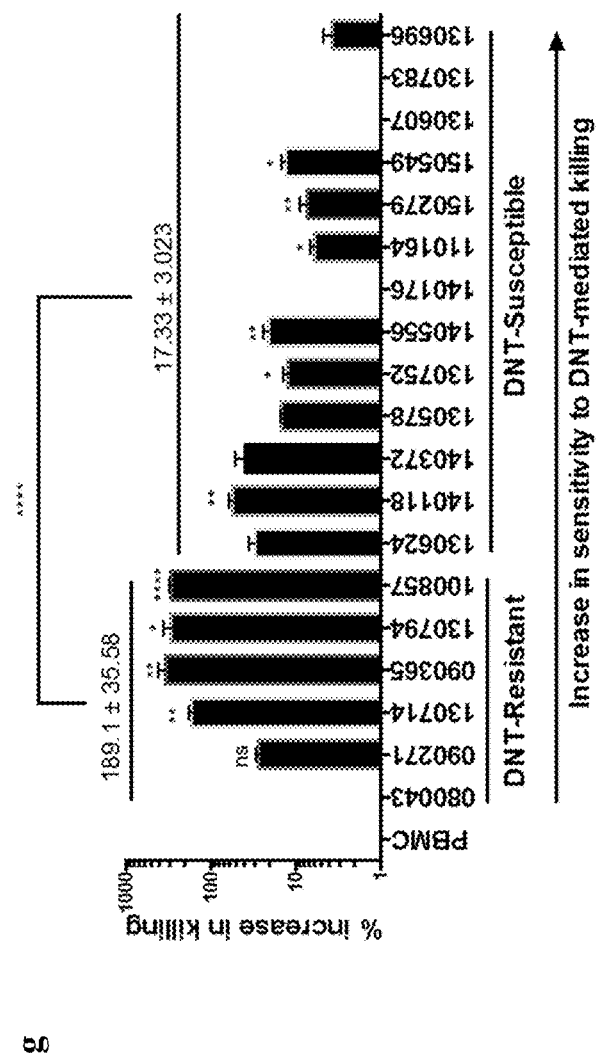

The results represent 3 independent experiments each with triplicates. (e-g) AML3/OCI, DNTs (e), primary AML samples, or allogeneic HD PBMCs (f and g) were pretreated or untreated with recombinant IFNγ (rIFNγ, 50 ng/ml) for 1 hour. Subsequently, AML cells or PBMCs were co-cultured with DNTs and % specific killing was determined as described above. The graphs shown are representative of 3, 4, 3, and 6 separate experiments for PBMC, AML3/OCI, DNT, and primary AML samples, respectively. g) % increase in DNT-mediated killing was determined with data shown in FIG. 3f. Number above represents the average % increase in killing ±SEM for DNT-resistant (n=6) or -susceptible (n=14) primary AML samples upon rIFNγ pretreatment. n.s. not significant. *, p<0.05; , p<0.01; *, p<0.001;****, p<0.0001, using unpaired, two-tailed Student's t test or linear regression test.

Figure 4:
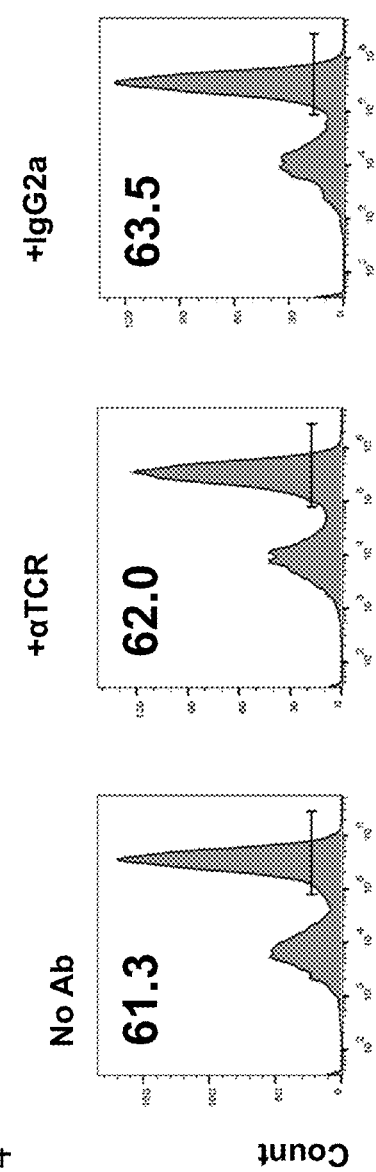
Figure 4:
Figure 4:
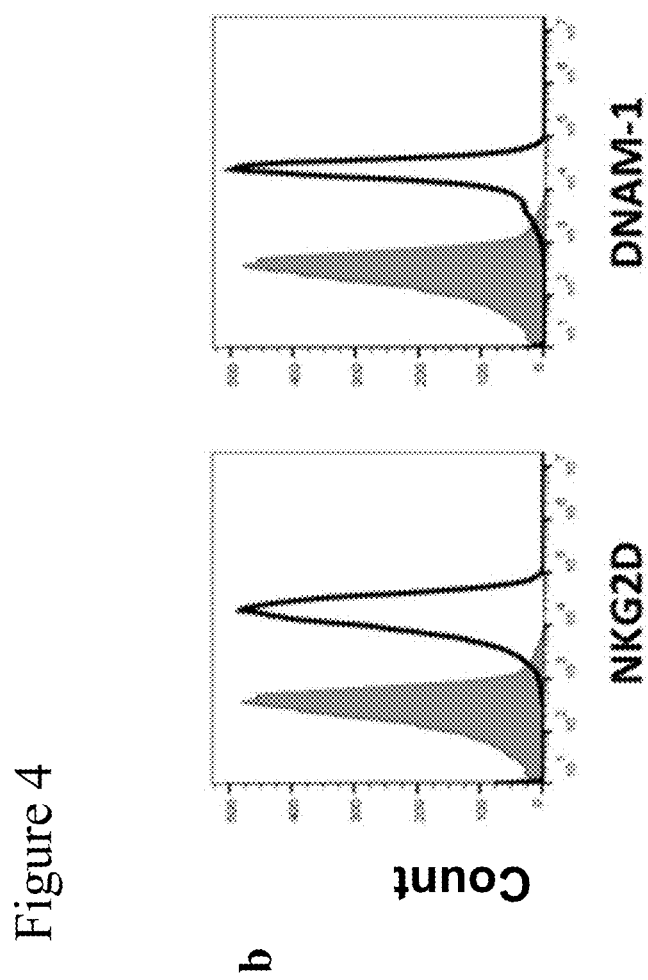
Figure 4:
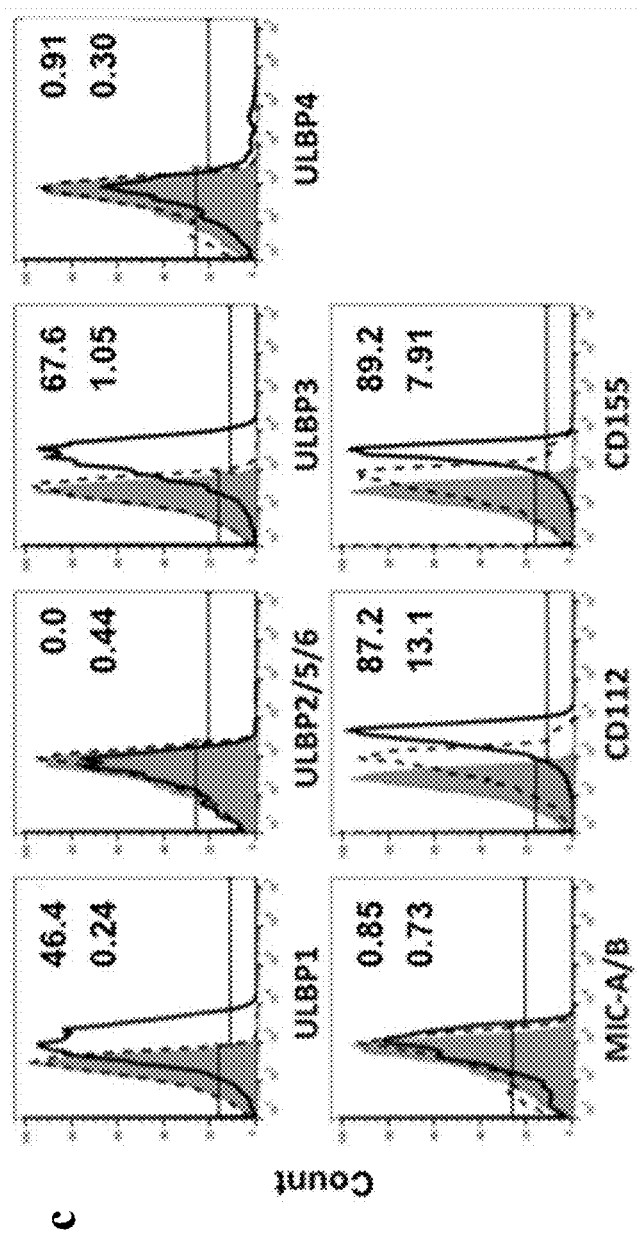
Figure 4:
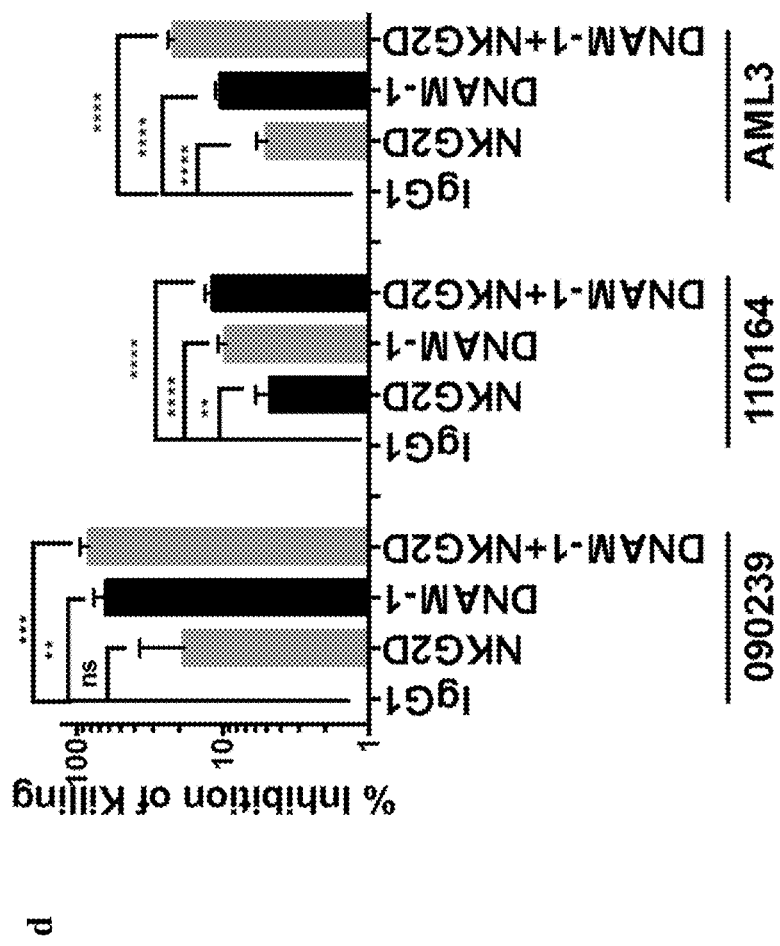
Figure 4:
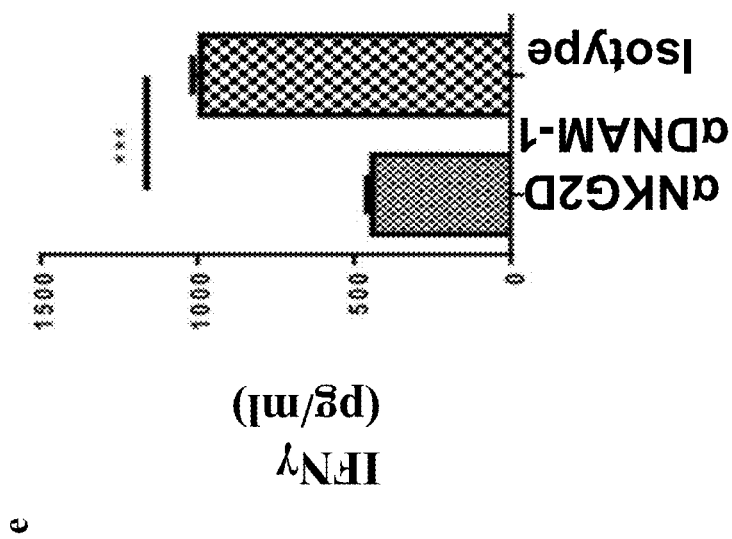

FIG. 4 shows DNTs kill AML cells in NKG2D– DNAM-1-dependent, but TCR-independent manner. (a) DNTs were pre-incubated with IgG2a isotype control or anti-TCRαβ and TCRγδ antibodies (10 μg/ml for each antibody) for 30 min before co-culture with Jurkat, AML3/OCI cells or primary AML cells (140012, 080009, and 110164) at 4-to-1 DNT-to-target ratio for 2 hours. % specific killing was determined as above. The graphs represent the results from 4 independent experiments. The histograms represent the results from three independent experiments against AML3/OCI cells. (b) Ex vivo expanded DNTs were stained with DNAM-1 and NKG2D antibodies. Filled histograms represent FMO controls. The graphs shown are representative of DNTs expanded from three different donors. (c) Primary AML patient blasts (solid line) and PBMCs from HDs (dotted line) was stained with NKG2D ligands ULBP-1, ULBP-2/5/6, ULBP-3, ULBP-4, and MIC-A/B, and DNAM-1 ligands CD155 and CD112. Filled histograms represent FMO controls. Numbers shown are % cells that expressed corresponding ligands by AML blasts (top) or normal PBMCs (bottom). (d) DNTs were pre-incubated with IgG2a or IgG1 isotype controls, anti-NKG2D, DNAM-1 or NKG2D+DNAM-1 blocking antibodies for 1 hour before co-cultured with primary AML blasts (090239 and 110164) or OCI/AML3 cell line and % inhibition of killing was determined as described in FIG. 3e. Experiments were done in triplicates and representative data from 4 separate experiments for OCI/AML3 is shown. (e) Level of IFNγ release from DNT-AML cell co-culture in the presence of NKG2D and DNAM-1 blocking antibodies or IgG1 isotype control. Data shown are representative of two independent experiments. p<0.01, *p<0.001.

Figure 5:
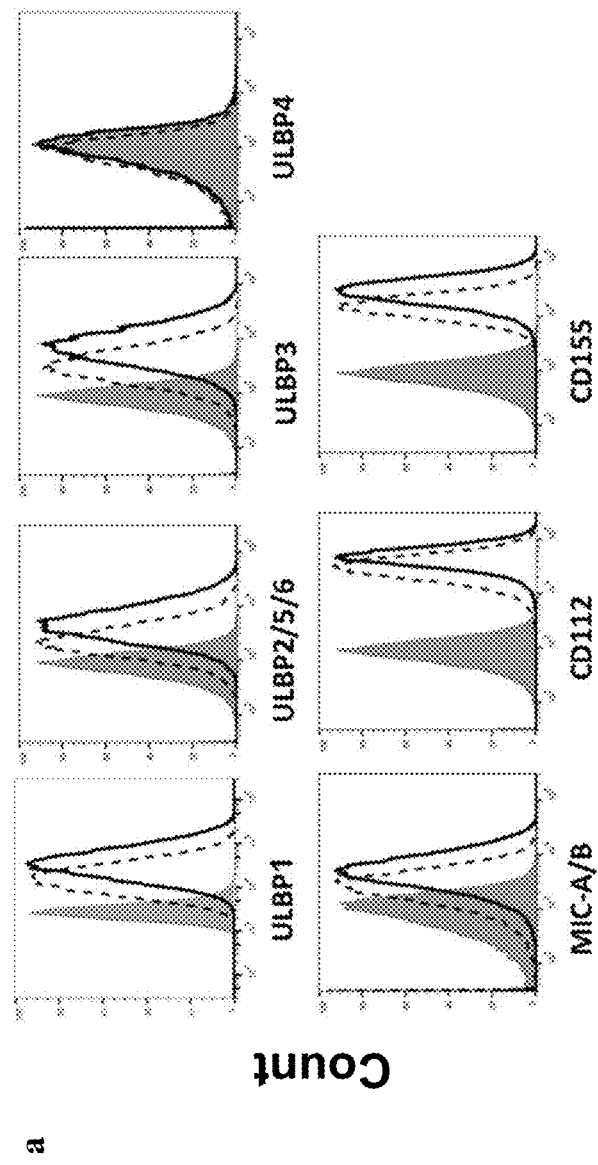
Figure 5:
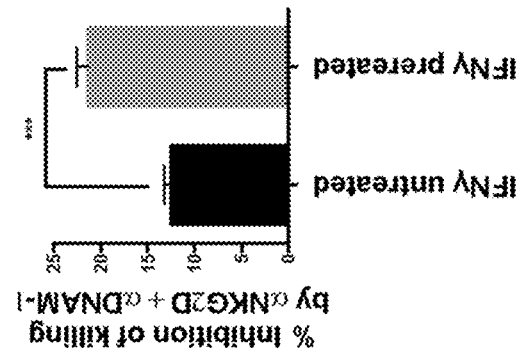
Figure 5:
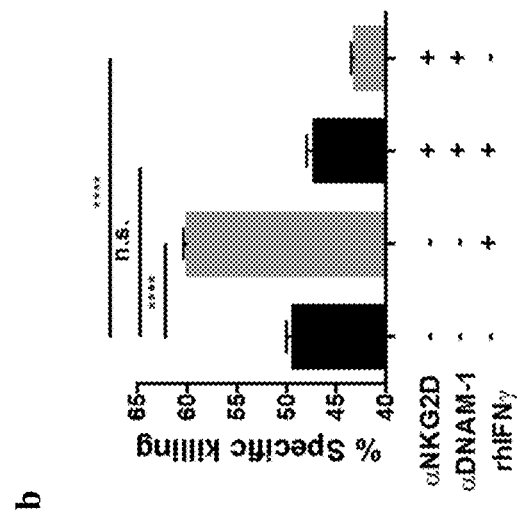

FIG. 5 shows IFNγ increases NKG2D and DNAM-1 ligands expression on AML cells and enhances their susceptibility to DNT-induced apoptosis. a) AML3/OCI cells were incubated with (solid lines) or without (dotted lines) 50 ng/ml rIFNγ overnight and their expression of NKG2D and DNAM-1 ligands is shown. Filled histograms represent FMO controls. Graphs are representative of 4 separate experiments done with 3 AML cell lines AML3/OCI, KG1a, and MV4-11. (b and c) AML3/OCI were pretreated or untreated with rIFNγ (50 ng/ml) then co-cultured with DNTs in the presence of 10 μg/ml anti-NKG2D and DNAM-1 blocking antibodies or isotype control antibody, when blocking antibodies were not used. % specific killing of targets from each treatment are shown (b). % inhibition of DNT-mediated cytotoxicity by anti-NKG2D and DNAM-1 antibodies in a killing assay conducted against IFNγ-pretreated and untreated targets was calculated as described in Methods section (c). Results represent 4 separate experiments each with triplicates. *, p<0.001;**, p<0.0001, using unpaired, two-tailed Student's t test.

Figure 6:
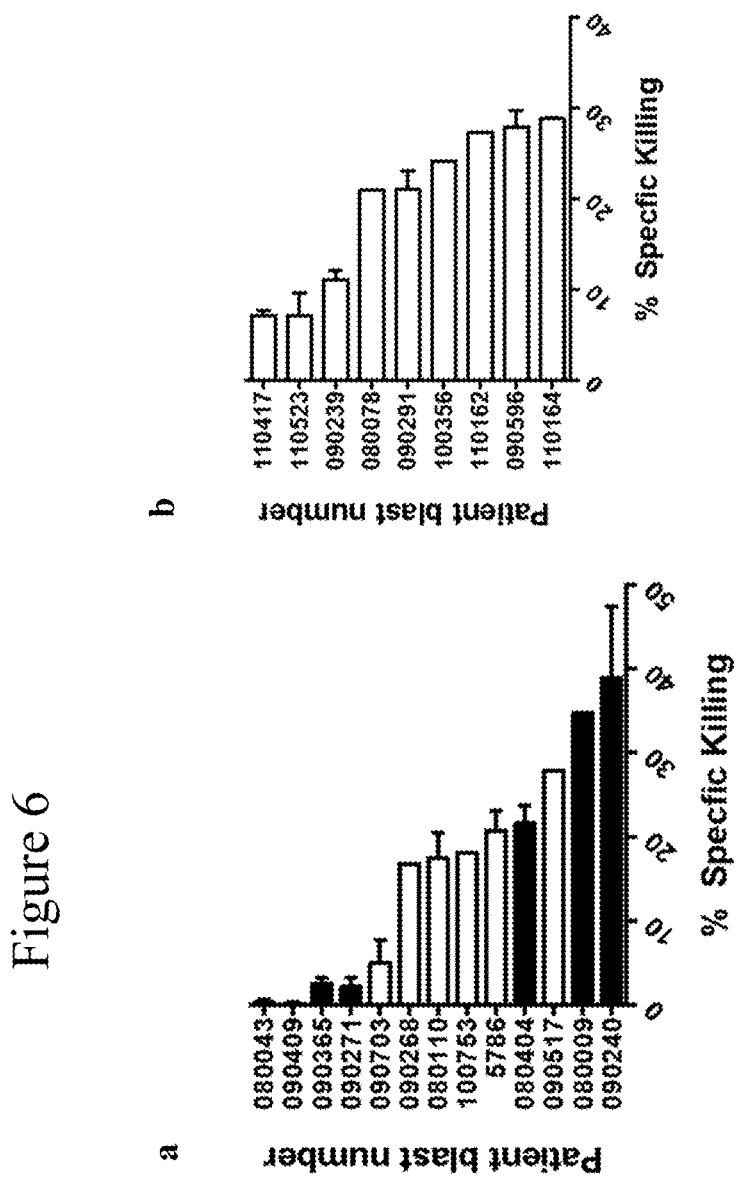
Figure 6:
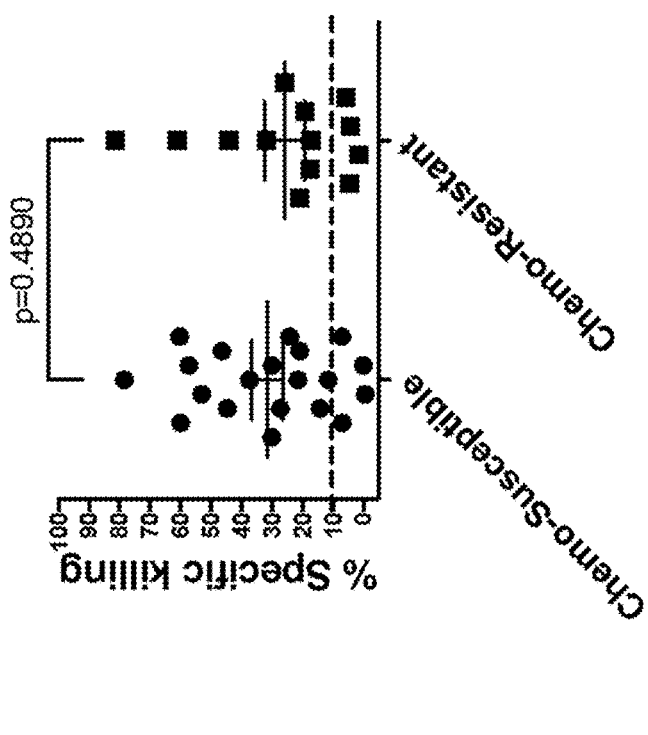
Figure 6:
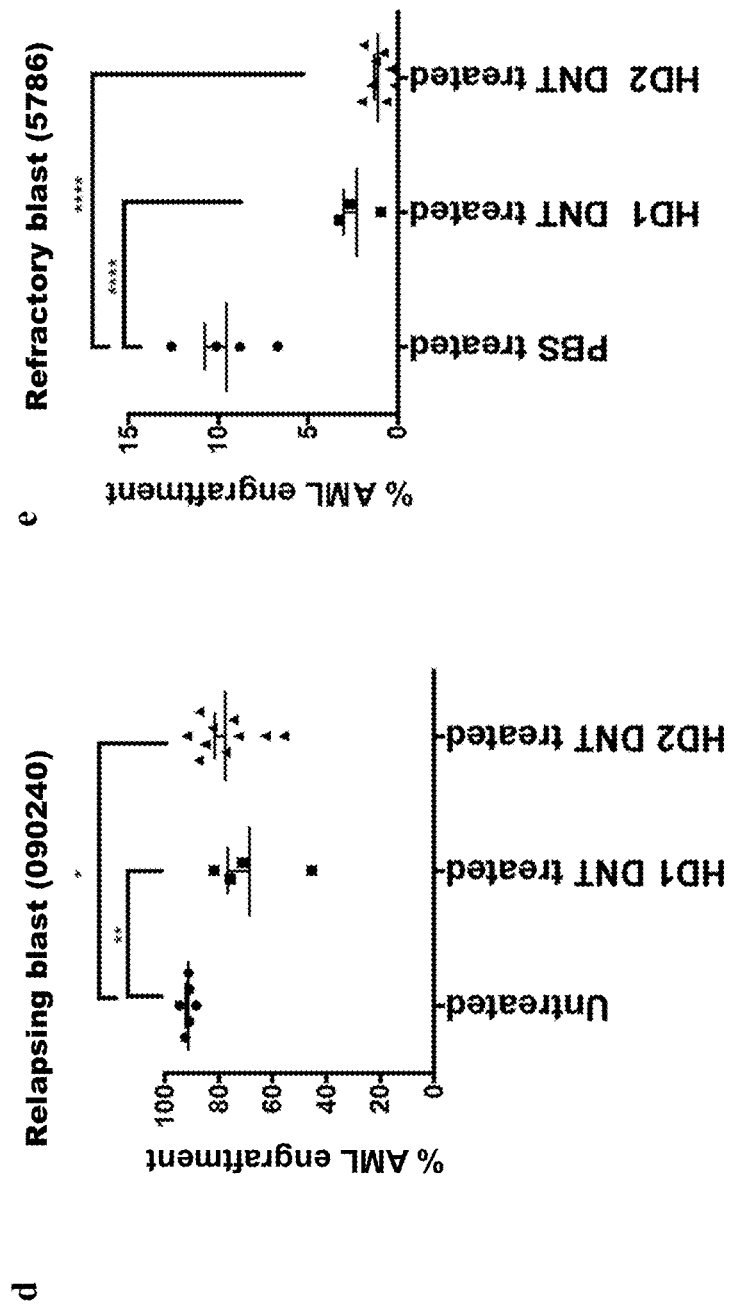
Figure 6:
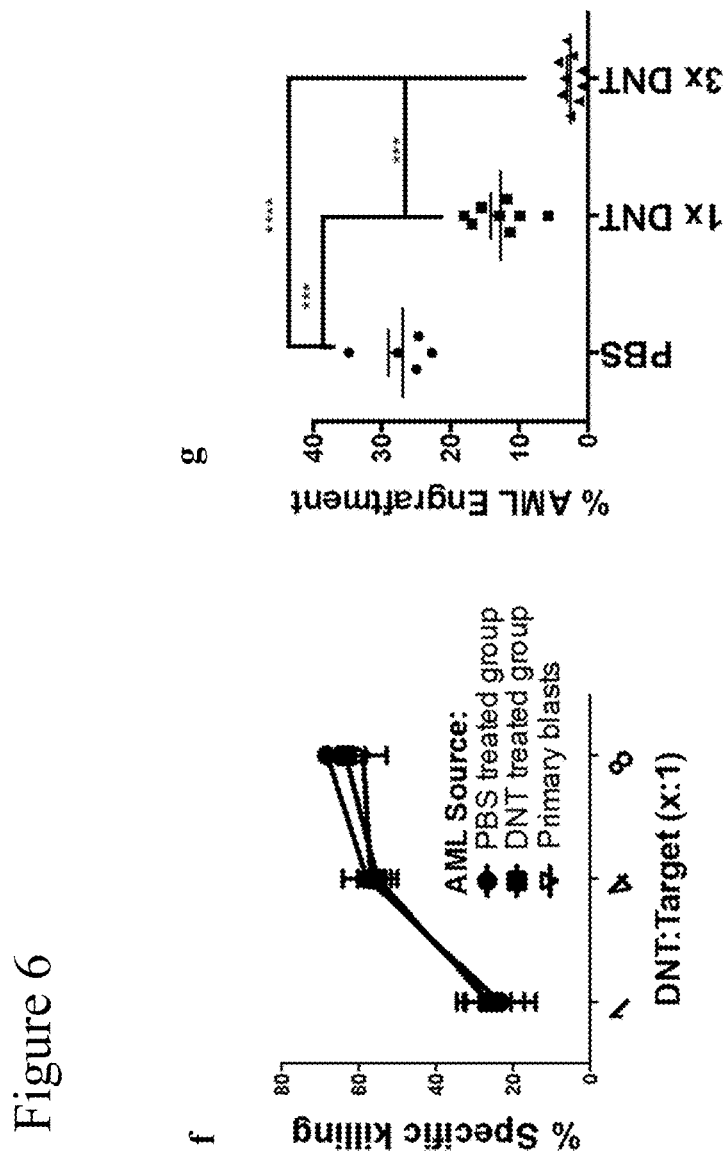
Figure 6:
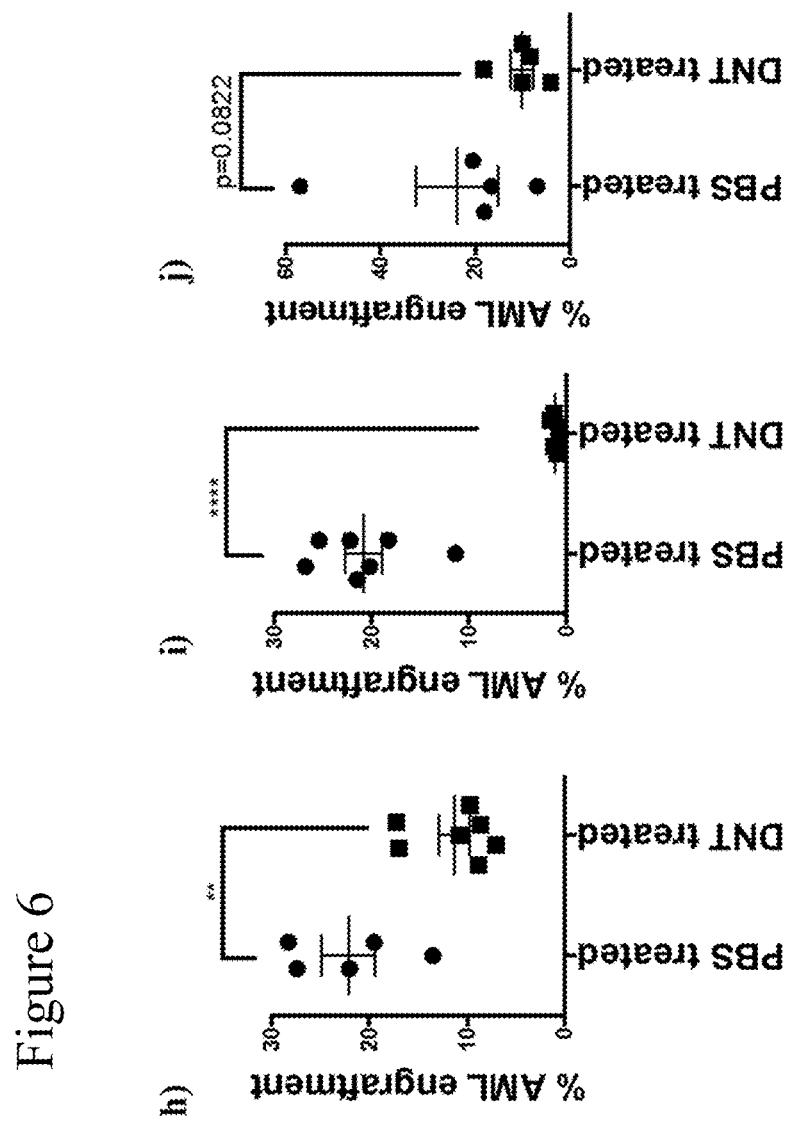

FIG. 6 shows DNTs can effectively target chemotherapy-resistant primary AML blasts in vitro and in vivo. (a and b) Cytotoxicity of DNTs expanded from HDs against primary (a) chemotherapy resistant AML cells (black bars) obtained from refractory or relapsing patients and (b) chemotherapy-susceptible AML cells determined by the 2-hour flow based killing assay. (c) The level of in vitro susceptibility of chemotherapy-susceptible (n=20) and -resistant (n=13) primary AML samples to DNT-mediated cytotoxicity was compared. AML samples from chemotherapy-susceptible and -resistant patients show a similar level of average sensitivity to anti-leukemic activity mediated by DNTs. (d and e) Sublethally irradiated NSG mice were intrafemorally injected with 2.5-5×10$^6$ cells/mouse of primary AML blasts from chemotherapy resistant relapsing (d; 090240) or refractory (e; 5786) patients. 10 days post blast injection, mice were injected with PBS or 2×10$^7$ DNTs expanded from two different HDs. 39 days and 28 days post 090240 and 5786 blasts injection, respectively, AML cells in spleen (d) or BM (e) were detected by gating on human CD33$^+$ and CD45$^+$ cells by flow cytometry. Each dot represents the data from one mouse and horizontal bars represent the mean values and the error bars represent SEM of each group. (f) Residual AML blasts (090240) obtained from each treatment group (n=4) was collected and used as targets in vitro. The primary AML blasts used for the initial engraftment were used as a control and DNTs expanded from the same donor for the in vivo experiment was used as effectors in in vitro killing assay. (g) NSG mice engrafted with 2.5×10$^6$ primary blasts 090543 was infused with PBS (n=5), single injection of 2×10$^7$ DNTs on day 3 post blast injection (n=8) or three injections of 2×10$^7$ DNTs on day 3, 7 and 11 post blast injection (n=9). 32 days post AML blast injection, mice were sacrificed and AML engraftment was analyzed as described above. (h-j) NSG mice injected with primary AML blasts obtained from 3 chemotherapy-resistant AML patients 090517 (h), 090295 (i), and 090428 (j)) were treated with 3 injections of 2×10$^7$ DNTs on day 3, 6, and 10 post AML injection. 23 days post blast injection, AML cells in BM were detected as described above. Each dot represents result from one mouse and horizontal bars represent the mean values and the error bars represent SEM of each group. *, p<0.05; , p<0.01; *, p<0.001;****, p<0.0001, using unpaired, two-tailed Student's t test.

Figure 7:
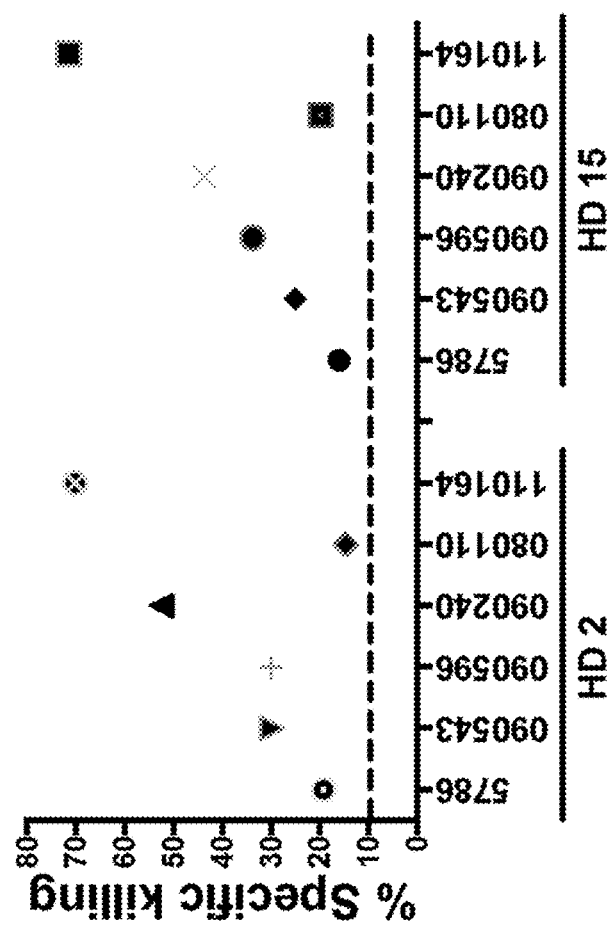

FIG. 7 shows DNTs expanded from different HDs have comparable level of cytotoxicity. Killing assay performed using DNTs expanded from 2 different HDs (HD2 and HD15) against 6 primary AML samples (shown in different symbols) as described in FIG. 3. Each symbol represents the level of killing induced by a different HD DNT.

Figure 8:
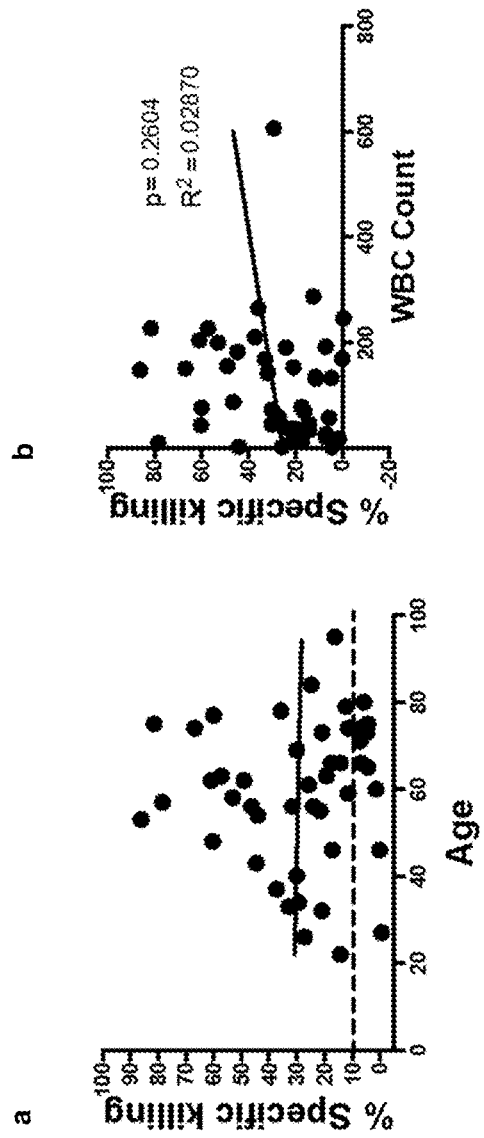
Figure 8:
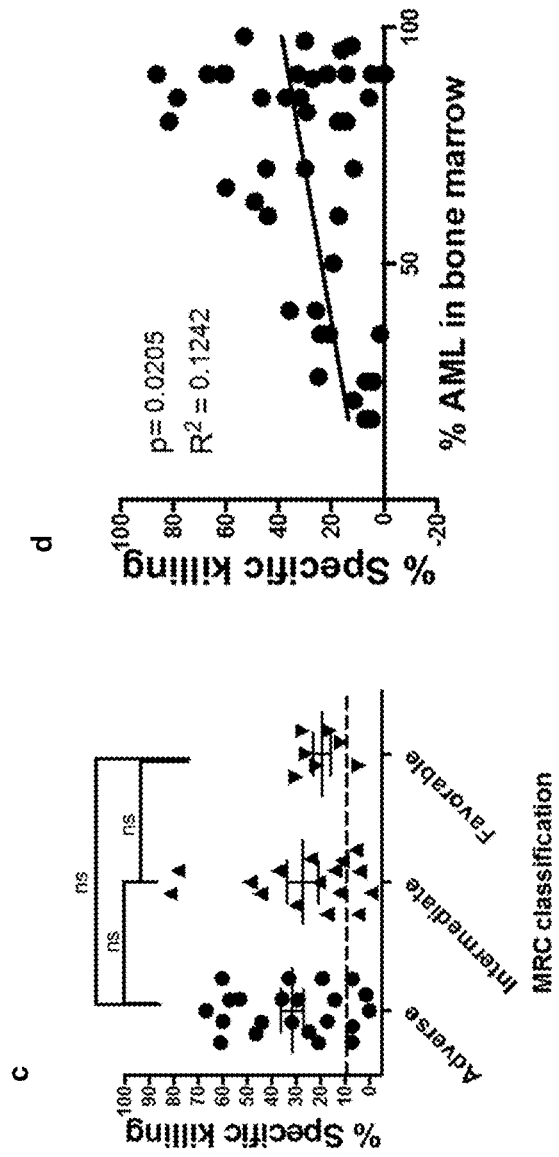
Figure 8:
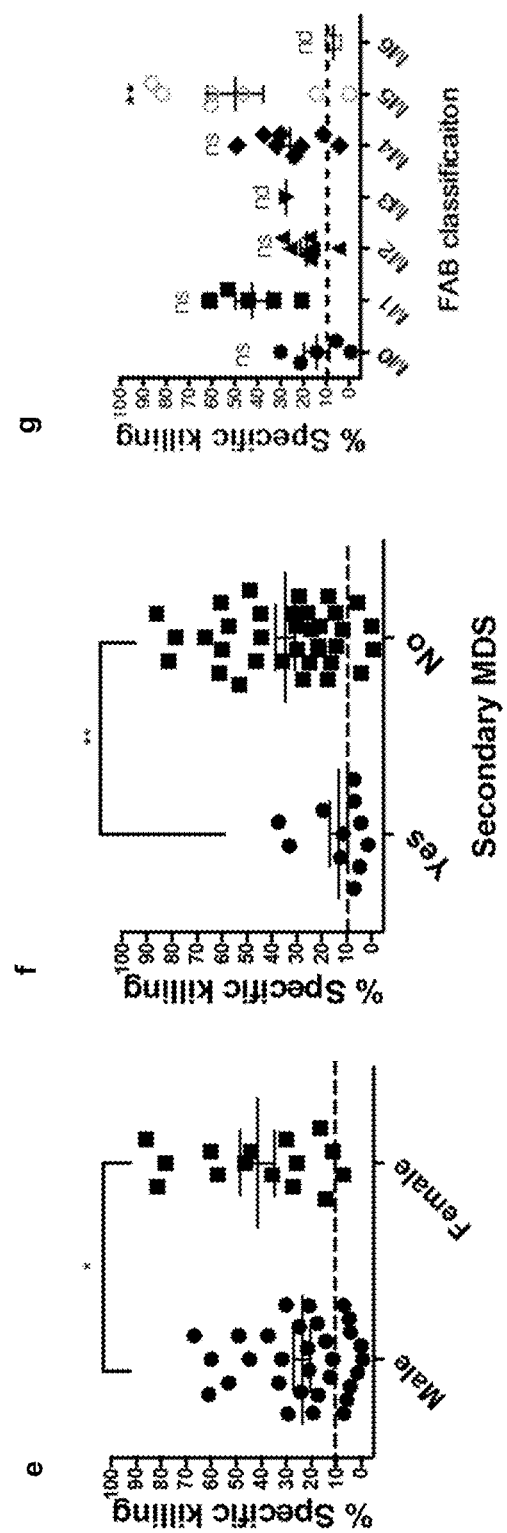

FIG. 8 shows Correlation between the susceptibility of AML patient blasts to DNT-mediated cytotoxicity and clinical features. The susceptibility of primary blast samples to DNT-mediated cytotoxicity in vitro determined as described above. (a, b and c) The correlation between the level of susceptibility of each patient's AML blasts to DNT-mediated cytotoxicity in vitro and their age (a; n=46), WBC count (b, n=46), and % AML cells in BM (d, n=43) were determined by linear regression test. (c, e and f). The levels of AML blast susceptibility to DNTs grouped by patient MRC cytogenetics risk classification (c, n=45), sex (d, n=46), or myelodysplastic syndrome (MDS) subtypes (f, n=46) were compared. g) Samples were grouped based on patients FAB classification, and each group was compared to the overall average % specific killing from rest of the patient samples tested. Unpaired, two-tailed Student's t test was used. Each dot represents average % specific killing of a single blast sample *, p<0.05; **, p<0.01; p<0.0001; ns, not significant, nd, not done.

DETAILED DESCRIPTION

In the Following Description, Numerous Specific Details are Set Forth to Provide a Thorough Understanding of the Invention. However, it is Understood that the Invention May be Practiced without these Specific Details.

Acute myeloid leukemia (AML) is a disease with poor long-term patient survival. While chemotherapies are effective in inducing remission, chemotherapy-resistant disease and relapse hampers better clinical outcome. Here, we show that allogeneic double negative T cells (DNTs) are cytotoxic against both chemotherapy-resistant and -susceptible AML cells in vitro and in AML-xenograft mouse models. Importantly, allogeneic DNTs are not cytotoxic to normal peripheral blood mononuclear cells or hematopoietic progenitor/stem cells, nor do they cause xenogeneic graft-versus-host disease in mice. Inhibition of NKG2D or DNAM-1, but not the T cell receptor, suppressed DNT-mediated cytotoxicity against AML cells. Upon encountering AML cells, DNTs released IFNγ which upregulated expression of ligands to NKG2D and DNAM-1 on tumor cells increasing their susceptibility to DNT-mediated cytotoxicity. Collectively, this study demonstrates the safety and efficacy of allogeneic DNTs as a potential new immunotherapy for AML and identifies molecules important for mediating anti-leukemia activities of DNTs.

In an aspect, there is provided a method of treating leukemia or lymphoma in a subject in need thereof, comprising administering to the subject an effective amount of double negative T cells (DNTs) and Interferon-γ.

As used herein, "effective amount" or "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects. For purposes of Interferon-γ, for example, an effective amount can include dosing at levels of 0.1, 0.25, 0.5, and 1.0 mg/m$^2$ per day (see for example R. M. Stone et al. "Recombinant Human Gamma Interferon Administered by Continuous Intravenous Infusion in Acute Myelogenous Leukemia and Myelodysplastic Syndromes" Am J. Clin Oncol 16(2) 159-163 1993), which is incorporated herein by reference. In another example, Interferon-γ can be injected S.C. from 20-50 ug from about twice a week to about every other day, for high risk AML patients.

As used herein, the term "cancer" refers to one of a group of diseases caused by the uncontrolled, abnormal growth of cells that can spread to adjoining tissues or other parts of the body. Cancer cells can form a solid tumor, in which the cancer cells are massed together, or exist as dispersed cells, as in leukemia. The term "cancer cell" refers a cell characterized by uncontrolled, abnormal growth and the ability to invade another tissue or a cell derived from such a cell. Cancer cells include, for example, a primary cancer cell obtained from a patient with cancer or cell line derived from such a cell. In one embodiment, the cancer cell is a hematological cancer cell such as a leukemic cell or a lymphoma cell. For example, in one embodiment the cancer cell may be a leukemic cell from a subject with AML or a lymphoma cell such as a cell from a subject with Non-Hodgkin Lymphoma (NHL). In one embodiment, the cancer cell may be a leukemic cancer cell in a subject with AML. In one embodiment, the DNTs described herein may be used to inhibit the growth or proliferation of cancer cells in vitro, ex vivo or in vivo. In one embodiment, the DNTs described herein may be used to kill cancer cells in vitro, ex vivo or in vivo.

The term "leukemia" as used herein refers to any disease involving the progressive proliferation of abnormal leukocytes found in hematopoietic tissues, other organs and usually in the blood in increased numbers. "Leukemic cells" refers to leukocytes characterized by an increased abnormal proliferation of such cells.

As used herein, "acute myeloid leukemia" ("AML") refers to a cancer of the myeloid line of blood cells, characterized by the rapid growth of abnormal white blood cells that accumulate in the bone marrow and interfere with the production of normal blood cells.

As used herein, "chronic myeloid leukemia" ("CML") refers to a cancer characterized by the increased and unregulated growth of predominantly myeloid cells in the bone marrow and the accumulation of these cells in the blood.

As used herein, "lymphoma" refers to disease characterized by blood cell tumors that develop from lymphatic cells. Optionally, lymphoma may be Hodgkin Lymphoma (HL) or a non-Hodgkin lymphoma (NHL). Examples of NHL include Burkitt's lymphoma and T cell lymphoma. "Lymphoma cells" refer to lymphocytes characterized by an increased abnormal proliferation of such cells.

The term "subject" as used herein includes all members of the animal kingdom including mammals, and suitably refers to humans. Optionally, the term "subject" includes mammals that have been diagnosed with cancer or are in remission. In one embodiment, the term "subject" refers to a human having, or suspecting of having, a hematological cancer. In one embodiment, the term "subject" refer to a human having AML or suspected of having AML, optionally recurrent or relapsing AML.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease (e.g. maintaining a patient in remission), preventing disease or preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment.

In different embodiments, the double negative T cells (DNTs) are administered either prior to, simultaneously or subsequent to the administration of Interferon-γ.

In an aspect, there is provided a method of treating leukemia or lymphoma in a subject in need thereof, comprising administering to the subject an effective amount of double negative T cells (DNTs), wherein the subject has previously been administered Interferon-γ.

In an aspect, there is provided a method of sensitizing a subject to the treatment of leukemia or lymphoma with double negative T cells (DNTs), comprising administering to the subject an effective amount of Interferon-γ.

The DNTs described herein may be readily obtained by a person of skill in the art and are readily distinguished from other kinds of T cells. In one embodiment, the DNTs do not express CD4 and CD8. In one embodiment, the DNTs express CD3-TCR complex and do not express CD4 and CD8. In some embodiments, the DNTs are CD4−CD8−, preferably expressing CD3-TCR complex; and further preferably have the phenotype CD3+, γδ-TCR+ or αβ-TcR+, CD4−, CD8−, α-GalCer-loaded-CD1d−, PD-1−, CTLA4−; CD3+, γδ-TCR+ or αβ-TcR+, CD4−, CD8−, α-GalCer-loaded CD1d, PD-1−, CTLA4−, CD44+, CD28−; CD3+, CD4−, CD8−, α-Gal−, PD-1−, CTLA4−, CD44+; or CD3+, CD4−, CD8−, α-GalCer-loaded-CD1d−, Jα24-Vα14 TCR−, CD44+, PD-1−, CTLA4−, CD45RO+.

In some embodiments, the majority of DNTs are those which are CD4−CD8−, and are γδ-TCR+.

In some embodiments, the majority of DNTs are those which are CD4−CD8−, and are αβ-TcR+.

In some embodiments, the leukemia is acute myeloid leukemia (AML).

In some embodiments, the DNTs are autologous. Optionally, the subject from which the autologous DNT's are obtained has one or more detectable cancer cells. In some embodiments, the subject from which the DNTs are obtained has previously been treated for cancer, optionally wherein the subject from which the DNTs are obtained is not in complete remission. In some embodiments, the DNTs are obtained from the subject prior to, during or after chemotherapy. In some embodiments, the DNTs are obtained from the subject after one or more rounds of chemotherapy.

In some embodiments, the DNTs are allogeneic. Optionally, the DNTs are from one or more individuals without cancer.

As used herein, the term "allogeneic" refers to cells which are originally obtained from a subject who is a different individual than the intended recipient of said cells, but who is of the same species as the recipient. Optionally, allogeneic cells may be cells from a cell culture. In a preferred embodiment, the DNTs are obtained from a healthy donor. As used herein the terms "healthy volunteer" ("HV") or "healthy donor" ("HD") refer to one or more subjects without cancer. In one embodiment, the healthy donor is a subject with no detectable cancer cells, such as a subject with no detectable leukemic cells.

In some embodiments, the DNTs are obtained from a sample comprising peripheral blood mononuclear cells (PBMC). Optionally, the sample is a blood sample. Blood samples may be subjected to further processing. For example, leukapheresis may be performed on the sample to separate white blood cells.

In some embodiments, The method of any one of claims 1 to 18, wherein the DNTs have been expanded in vitro or ex vivo.

In some embodiments, the subject has recurrent, relapsing or refractory AML. Optionally, the recurrent or relapsing AML is caused by minimal residual disease (MRD) or leukemic stem cells.

In some embodiments, the DNTs are administered to the subject by intravenous injection.

In some embodiments, the DNTs are administered to the subject prior to, during or after chemotherapy. Optionally, the DNTs are administered to the subject the same day, within 3 days, within 1 week, within 2 weeks, within 3 weeks or within 1 month of chemotherapy.

In some embodiments, the method further comprises administering to the subject one or more additional doses of an effective amount of DNTs. Optionally, the additional doses are administered at least 3 days after the last dose of DNTs, at least 5 days after the last dose of DNTs, or optionally between 3 days and two weeks after the last dose of DNTs.

In an aspect, there is provided a method of sensitizing leukemic or lymphoma cells to double negative T cells (DNTs) therapy, comprising exposing the cells to Interferon-γ.

In an aspect, there is provided a method of inhibiting the growth or proliferation of leukemia or lymphoma comprising exposing the leukemic or lymphoma cells to double negative T cells (DNTs) and Interferon-γ.

As used herein, "reducing the growth or proliferation of a cancer cell" refers to a reduction in the number of cells that arise from a cancer cell as a result of cell growth or cell division and includes cell death. The term "cell death" as used herein includes all forms of killing a cell including necrosis and apoptosis. As used herein, "chemotherapy-resistant cancer" refers to cancers that do not respond to treatment with chemotherapy or that relapses following treatment with chemotherapy. For example, chemo-resistant cells may be primary cancer cells obtained from subjects who do not respond to chemotherapy or cancer cells obtained from subjects who have initially responded to chemo and into remission but experience relapse of the disease. In some subjects, after relapse, the cancer cells no longer respond to chemotherapy and said subjects have chemotherapy-resistant cancer. In one embodiment, chemo-resistant cells are primary leukemic cells directly obtained from subjects.

In an aspect, there is provided a use of an effective amount of double negative T cells (DNTs) and Interferon-γ for treating leukemia or lymphoma in a subject in need thereof.

In an aspect, there is provided a use of an effective amount of double negative T cells (DNTs) for treating leukemia or lymphoma in a subject in need thereof and that has been administered Interferon-γ.

In an aspect, there is provided a use of an effective amount of Interferon-γ for sensitizing a subject to the treatment of leukemia or lymphoma with double negative T cells (DNTs).

In an aspect, there is provided a use of an effective amount of double negative T cells (DNTs) and Interferon-γ for inhibiting the growth or proliferation of leukemic or lymphoma cells.

In an aspect, there is provided a use of an effective amount of Interferon-γ for sensitizing leukemic or lymphoma cells to double negative T cells (DNTs) therapy.

In an aspect, there is provided a use of Interferon-γ in the preparation of a medicament for the combination treatment of leukemic or lymphoma cells with double negative T cells (DNTs).

In an aspect, there is provided a pharmaceutical composition comprising double negative T cells (DNTs) and Interferon-γ.

DNTs and/or Interferon-γ may be formulated for use or prepared for administration to a subject using pharmaceutically acceptable formulations known in the art. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The term "pharmaceutically acceptable" means compatible with the treatment of animals, in particular, humans. As used herein, "pharmaceutically acceptable carrier" means any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

The advantages of the present invention are further illustrated by the following examples. The examples and their particular details set forth herein are presented for illustration only and should not be construed as a limitation on the claims of the present invention.

EXAMPLES

Materials and Methods
DNTs and Leukemic Cell Lines

DNTs were enriched by depleting $CD4^+$ and $CD8^+$ cells from PBMCs and expanded ex vivo as previously described[17]. Briefly, isolated DNTs were cultured in anti-CD3 antibody coated plates (OKT3; 5 ng/ml) for 3 days in RPMI-1640 supplemented with 10% FBS and 250 IU/ml of IL2 (Proleukin); soluble anti-CD3 (0.1 ug/ml) was added on day 7. On days 3, 7 and 10, fresh media and IL-2 were added. The leukemic cell lines OCI/AML-3 (AML-3), and KG1a were obtained from ATCC.

Ethics Statement

Human blood, BM, and CD34+ cells were collected from healthy adult donors and AML patients after obtaining written informed consent and used according to University Health Network (UHN) Research Ethics Board and NHLBI approved protocols. Animal studies were approved by the institutional Animal Care Committee of the UHN (Permit Number: 741.22), and carried out in accordance with the Canadian Council on Animal Care Guidelines.

Antibodies, Flow Cytometry and ELISA

The following anti-human antibodies were used for cell staining: CD3-FITC or -PECy7, CD4-FITC or -PE, CD8-FITC or -PE, CD34-FITC or -PE, CD33-APC or -PECy5, CD56-PE, iNKT TCR (Vα24-Jα18 TCR)-APC or pan-αβ TCR-APC were purchased from Biolegend. Pan γδ-TCR-FITC was purchased from Beckman Coulter. Data acquisitions were performed using either BD Accuri C6 Flow cytometry (BD Bioscience) or LSRII (BD Biosciences) Flow cytometers and data were analyzed using FlowJo software (Tree Star, Inc.). Following antibodies were used for blocking assays: anti-human αβ-TCR (T10B9, BD Bioscience), γδ-TCR (B1, Biolegend), anti-NKG2D (1D11, Biolegend), anti-DNAM-1 (DX11, BD Pharmingen), or IFNγ (25718, R&D Systems) antibodies, and mouse IgG1 (MOPC-21, Biolegend) and IgG2a (MOPC-173, Biolegend) isotype controls at 10 µg/ml for 30 min. ELISA was conducted to determine the level of IFNγ produced by DNTs in different conditions.

Flow Cytometry Based In Vitro Killing Assay

DNTs stained with PKH-26 (Sigma) were co-cultured with target cells. After 2-4 hours of co-incubation, cells were stained with anti-human CD3-(HIT3a), CD33 (WM53), FITC-Annexin V and 7AAD (all from Biolegend), and analyzed using flow cytometry. Specific killing was calculated by:

$$\frac{(\% \ Annexin \ V^-_{with \ DNT} - 1/n \ Annexin \ V^+_{without \ DNT})}{100 - \% \ Annexin \ V^+_{without \ DNT}} \times 100.$$

For blocking assays, DNTs were incubated with neutralizing antibodies 30 min prior to co-incubation with target cell. % Inhibition of killing was calculated by $$\frac{(\% \ Specific \ Killing_{without \ Ab} - \% \ Specific \ Killing_{with \ Ab})}{\% \ Specific \ Killing_{without \ Ab}} \times 100.$$

For IFNγ pretreatment assay, DNTs or AML cells were pre-treated with 50 ng/ml of recombinant human IFNγ (Biolegend) for 1 hour or overnight.

Xenograft Models

NOD.Cg-Prkdcscid Il2rgtm1Wjl/SzJ (NSG) mice (Jackson Laboratories, Bar Harbor, Me.) were maintained at UHN animal facility. 8 to 12 week old females were irradiated (250 cGy) 24 hours prior to intrafemoral or tail vein injection of the 2-5×10$^6$ primary AML blasts. 2×10$^7$ DNTs were injected intravenously at the indicated time points. rIL2 (Proleukin, Novartis Pharmaceuticals, Canada) was administered (10$^4$ IU/mouse) IP concordant with the DNT injections on days 1, 2, 4, 7 and weekly thereafter where indicated. 2-4 weeks after last DNT injection, mice were sacrificed and spleen and bone marrow cells were harvested and frequency of AML was analyzed using flow cytometer. For GvHD study, DNT, PBS, or PBMC were injected into irradiated naïve NSG mice. For safety study, irradiated NSG mice were injected with 3×10$^5$ CD34$^+$CD133$^+$ HSPCs.

Statistical Analysis

All graphs and statistical analysis were generated using GraphPad Prism 5. Student's t test was used and *$p<0.05$; $p<0.01$; *$p<0.001$ indicate significance between experimental and control values. Error bars represent ±SEM Results and Discussion Ex Vivo Expanded Allogeneic DNTs Exert Potent Cytotoxic Activity Against Primary AML Patient Cells In Vitro and In Vivo.

Previously, we demonstrated that ex vivo expanded DNTs from peripheral blood of AML patients in complete remission were cytotoxic against autologous CD34$^+$ leukemic cells in vitro[17]. However, only about a third of the 36 DNT cultures initiated from 20 ml blood samples collected from 28 different patients with AML expanded successfully in vitro. Further, due to the presence of high leukemic blast counts, it was frequently challenging to isolate DNTs from patients with refractory or relapsing AML. To overcome these obstacles, we studied the potential to isolate and expand DNTs from 11 healthy donors (HDs) for their efficacy in targeting AML cells. DNTs were successfully expanded from all HDs at a median 10-fold higher average total number of cells (2.65±0.92×10$^8$ cells/20 ml blood) compared to AML patients (3.32±5.50×10$^7$ cells/20 ml blood) (FIG. 1a), and had significantly higher purity at culture harvest (90.74%±1.7% for HD DNTs vs. 65.0%±19.8% for patient DNTs) (FIG. 1b)

To determine whether allogeneic DNTs would efficiently target primary AML cells, the cytotoxicity of allogeneic DNTs expanded from HDs were studied against primary AML cells from 29 patients. We found heterogeneity in the level of cytotoxicity, but there was effective killing of AML cells obtained from 79% of patients after 2-hours co-culture with DNTs at 8-to-1 effector-to-target ratio (FIG. 1c). AML cells from the same patient showed similar levels of susceptibility to DNTs expanded from different donors (FIG. 7). No correlation was observed between the leukemic susceptibility to DNTs and patient-age at diagnosis or cytogenetic risk groups (FIGS. 8a and 8b), however there was a trend for reduced killing in samples obtained from male patients and patients with secondary myelodysplastic syndrome (FIGS. 8c and 8d).

Figure 1:
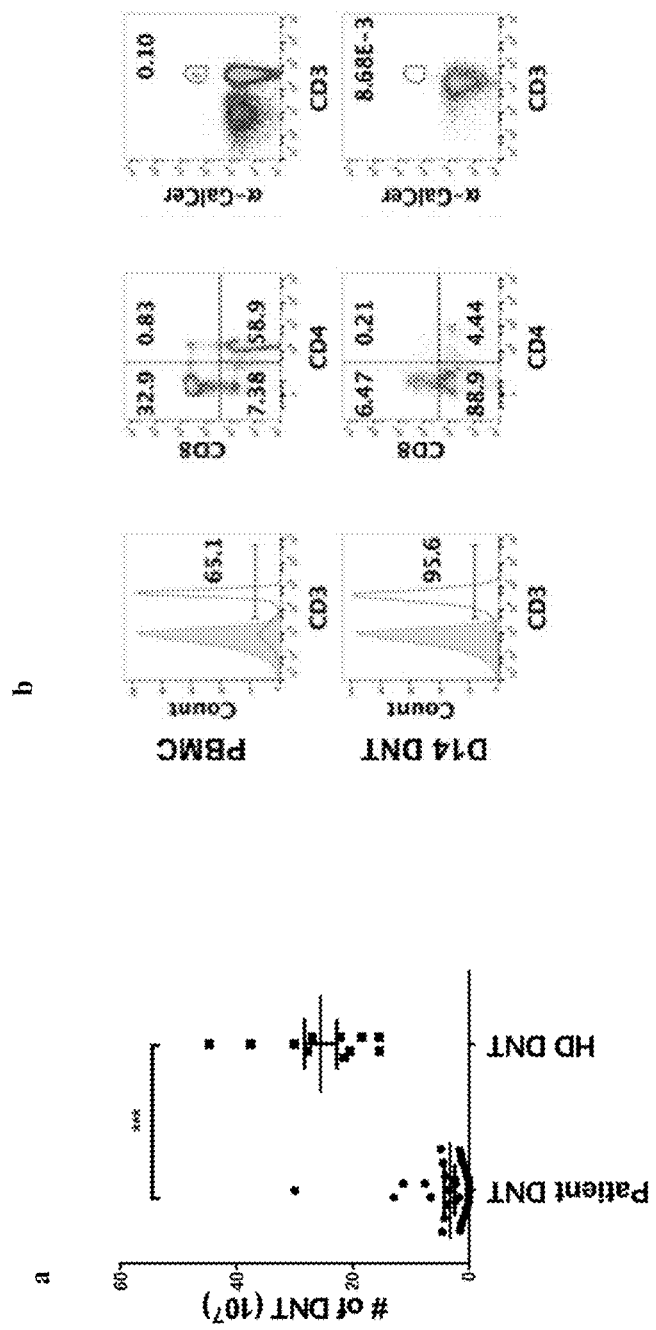
FIG. 1 shows Healthy donor (HD) DNTs can be expanded ex vivo and induce potent cytolytic activity against primary AML blasts in vitro and in vivo. (a) DNTs obtained from 20 ml PB from AML patients in chemotherapy-induced complete remission (n=34) or healthy donors (HD, n=11) were expanded for 14 days (b) Phenotypic characterization of PBMCs and DNTs post-expansion. PBMCs (top panels) or DNTs harvested 14 days after expansion (bottom panels) were stained with antibodies against human CD3, CD4, CD8, and αGalCer-CD1d tetramer. Filled histograms represent the fluorescence minus one (FMO) control. Numbers on the graphs represent the frequency of the population in each quadrant or gate. (c) Susceptibility of primary AML blasts obtained from 46 patients to DNT-mediated cytotoxicity was determined using 2-hour flow cytometry-based killing assay at 4-to-1 DNT-to-AML ratio. Effector DNTs were labeled with PKH-26 and AML blasts were defined as PKH-26− CD45$^{lo}$/CD33$^+$ population. Level of target cell death was determined by Annexin V and 7AAD staining. % Specific killing was determined by % Annexin V$^+$ AML cells in DNT-AML co-culture minus % Annexin V$^+$ target cell alone. ≤5% Annexin V$^+$ cells was considered as non-sensitive targets. (d) Schematic diagram of the AML-NSG xenograft model for determining the anti-leukemia activity of DNTs in vivo. Sublethally (250 Gy) irradiated NSG mice were intrafemorally injected with 2.5×10$^6$ primary AML blasts or PBS as a control. 10-14 days post blasts injection, mice were intravenously infused with 20×10$^6$ DNTs or PBS. 2-4 weeks after DNT treatment, spleen and bone marrows (BM) were harvested and the frequency of AML blasts were determined by staining the cells with anti-human CD45 and CD33 antibodies. (e) Representative dot plots show AML cells in mouse BM detected by gating on human CD33$^+$ and CD45$^+$ cells by flow cytometry. (f) Summary of the engraftment of 090392 AML cells in the BM of PBS- or DNT-treated mice. Each dot represents data from one mouse and horizontal bars represent the mean value and the error bars represent SEM of each group. This experiment was repeated with primary blasts from 4 different AML patients and DNTs expanded from 3 different HDs and similar results were obtained. (g) Summary of the anti-leukemic activity of allogeneic DNTs in a xenograft model. Primary AML sample and HD identification numbers are shown on the bottom. Each bar was compared to the mean percentage AML engraftment of PBS treated group. *p<0.05; p<0.01; *p<0.001
Figure 1:
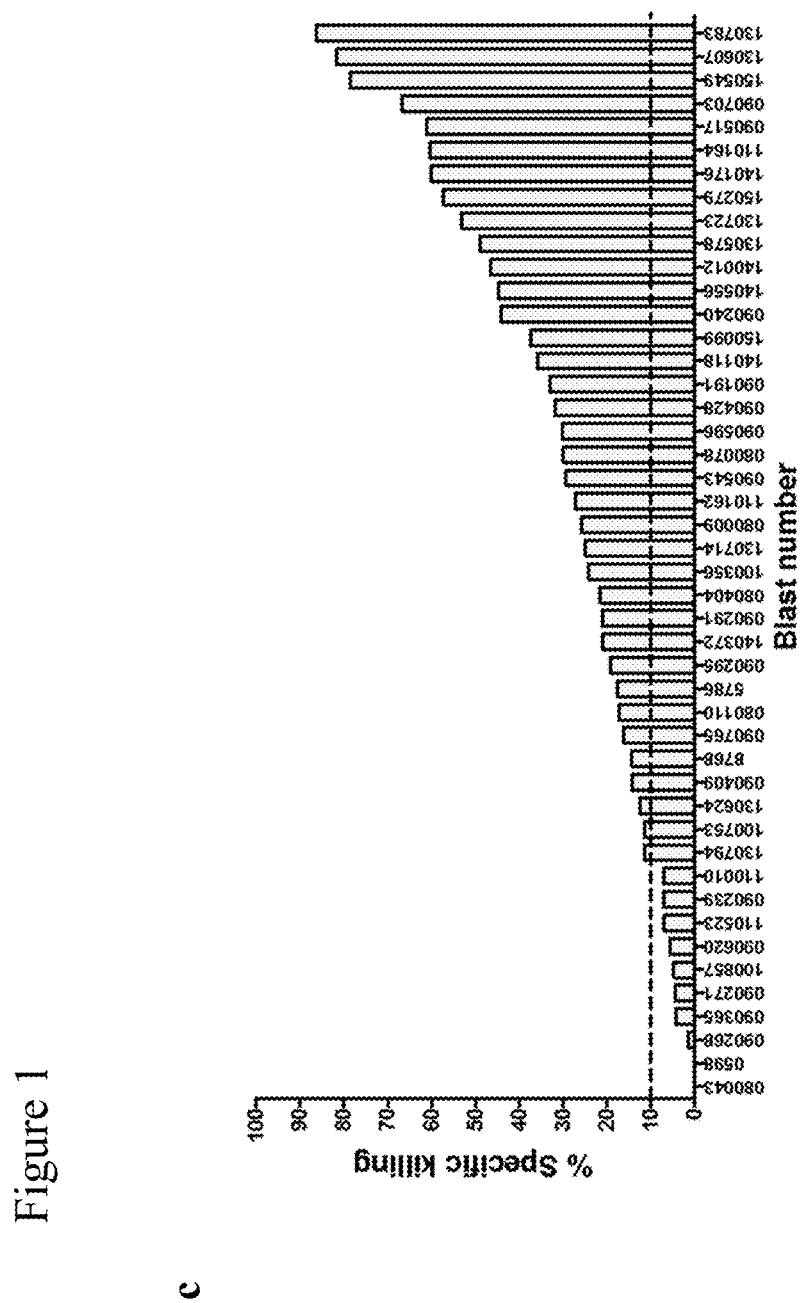
Figure 1:
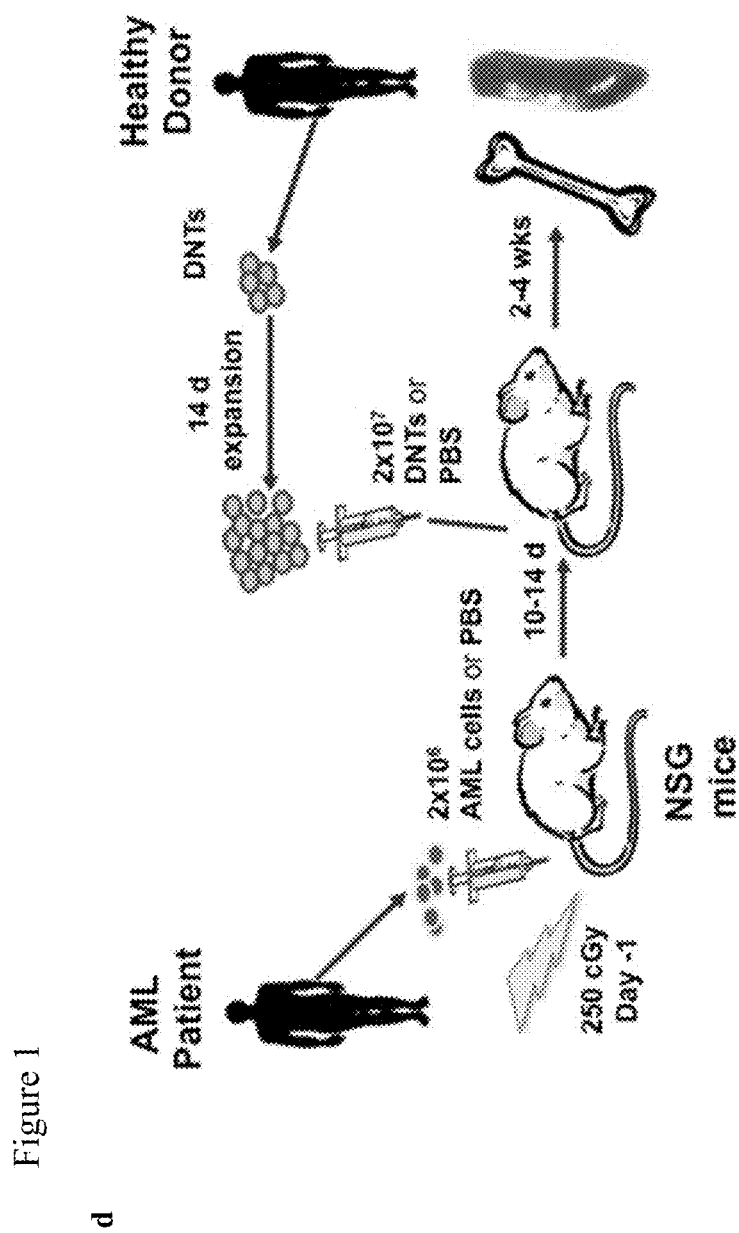
Figure 1:
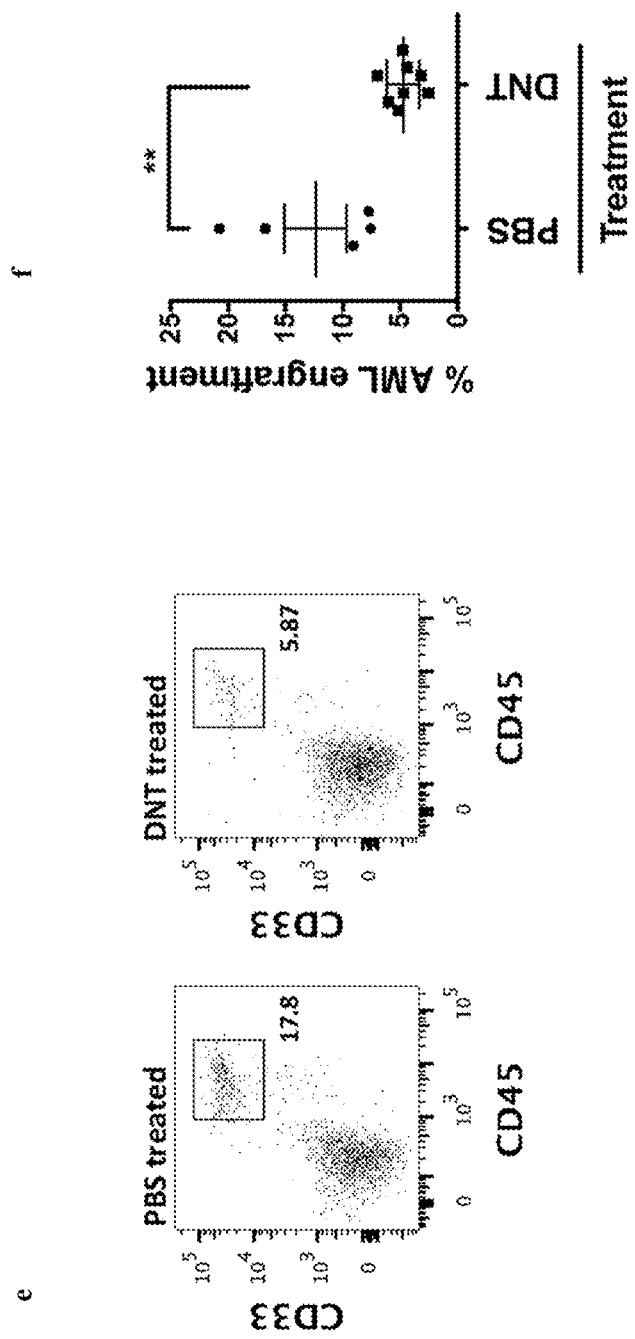
Figure 1:
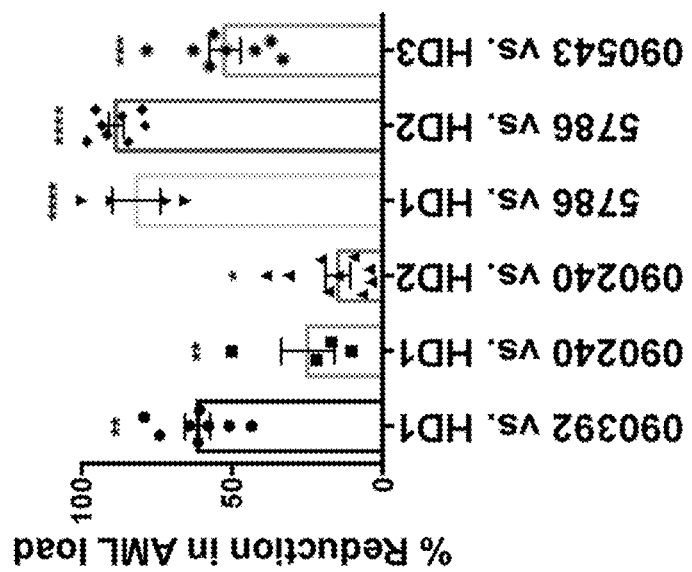

Since in vitro efficacy does not always correlate with in vivo effectiveness, we tested the anti-leukemia efficacy of DNTs using the gold standard xenograft AML model (FIG. 1d). NSG mice were engrafted with primary AML cell from 4 samples and after 14 days the animals were treated systemically with allogeneic DNTs expanded from different donors; the effect on AML engraftment was determined 2 weeks after the DNT injection. For one representative sample, a single injection of allogeneic DNTs derived from a HD significantly reduced leukemic cell engraftment in the bone marrow from 12.41%±2.69% to 4.75%±0.51% (FIGS. 1e and 1f) compared to untreated controls. Similar results were observed using three additional primary AML cells and DNTs expanded from two different donors (FIG. 1g). These data demonstrate that substantial numbers of DNTs can be expanded from HDs with high purity and that these expanded DNTs are cytotoxic to primary AML cells in vitro and appear to have the capacity to inhibiting AML in xenograft models after a single treatment.

Infusion of DNTs does not Cause GvHD Nor Kill Normal Allogeneic PBMCs and CD34$^+$ Hematopoietic Stem Cell Progenitors (HSPCs).

Figure 2:
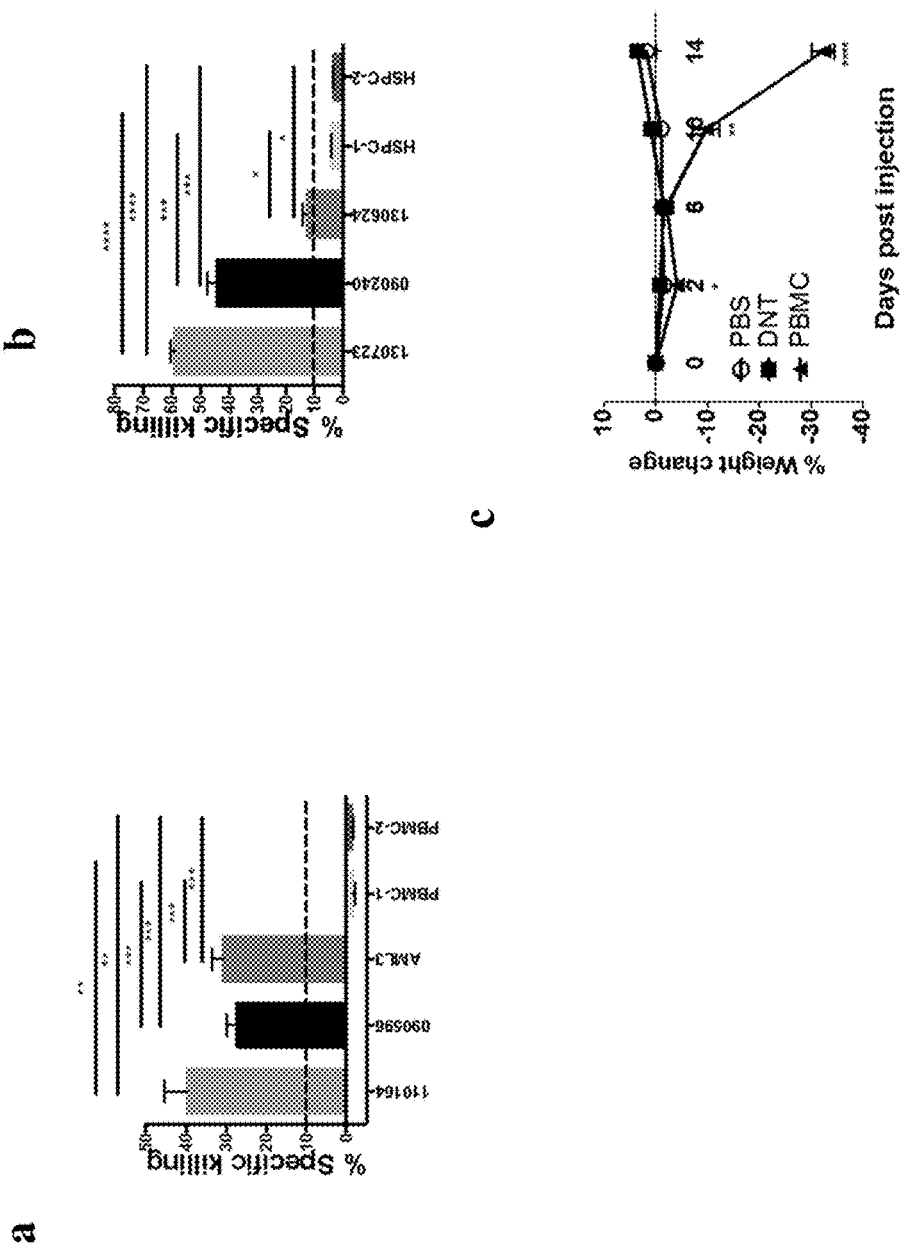
FIG. 2 shows Allogeneic DNTs do not kill normal cells in vitro and in vivo (a and b) Cytotoxicity of allogeneic DNTs expanded from 3 HDs against CD33$^+$ CD34$^-$ AML: AML3/OCI, primary AML patient blasts, 110164 and 090596, and normal allogeneic PBMCs from 2 different HDs (a) or CD33$^-$ CD34$^+$ AMLs: 130723, 090240, and 130624 and HSPCs from 2 different HDs (b) was determined at 4:1 effector-to-target ratio using the 2-hour flow-based killing assay as described in FIG. 1A. (c and d) Sublethally irradiated NSG mice were intravenously injected with PBS, 20×10$^6$ ex vivo expanded DNTs, or 5×10$^6$ human PBMCs obtained from 4 HDs (n=5 per group). c) On days 0, 2, 6, 10, and 14 after injection, mouse body weight was measured, and percentage weight loss was calculated as described in Methods section. The graph shown is a representative of results obtained using DNTs and PBMCs from 4 HDs. d) On day 14, mice were sacrificed and liver, lung, and small intestine were harvested and examined histologically via hematoxylin and eosin staining (20× magnification for liver and lung, 10× magnification for small intestine). The data shown are representative of results from each treatment group (PBS, DNT, and PBMC; n=3). (e and f) CD133$^+$ CD34$^+$ human HSPCs were intravenously injected into sublethally irradiated NSG mice (3×10$^5$ cells/mouse, n=13). 6-8 weeks post HSPC injection, 7 mice were intravenously injected with 1-2×10$^7$ ex vivo expanded allogeneic DNTs and the rest were injected with PBS. To determine chimerism originating from the HSPC population, cells from BM, spleen, and peripheral blood were obtained 8 weeks after DNT injection and stained with anti-mouse CD45, anti-human CD45, CD3, CD19, CD11b, CD56, CD33, and CD34 antibodies. The percentage of human leukocytes e) and its subsets f) were determined by flow cytometry analysis. Each dot represents % chimerism in one mouse, horizontal bars represent the mean and the error bars represent SEM of each group. The graphs shown are a representative of 3 independent experiments done with HSPCs from 2 HDs and allogeneic-DNTs expanded from 4 HDs. *, p<0.05; , p<0.01; *, p<0.001; ****, p<0.0001, using unpaired, two-tailed Student's t test.
Figure 2:
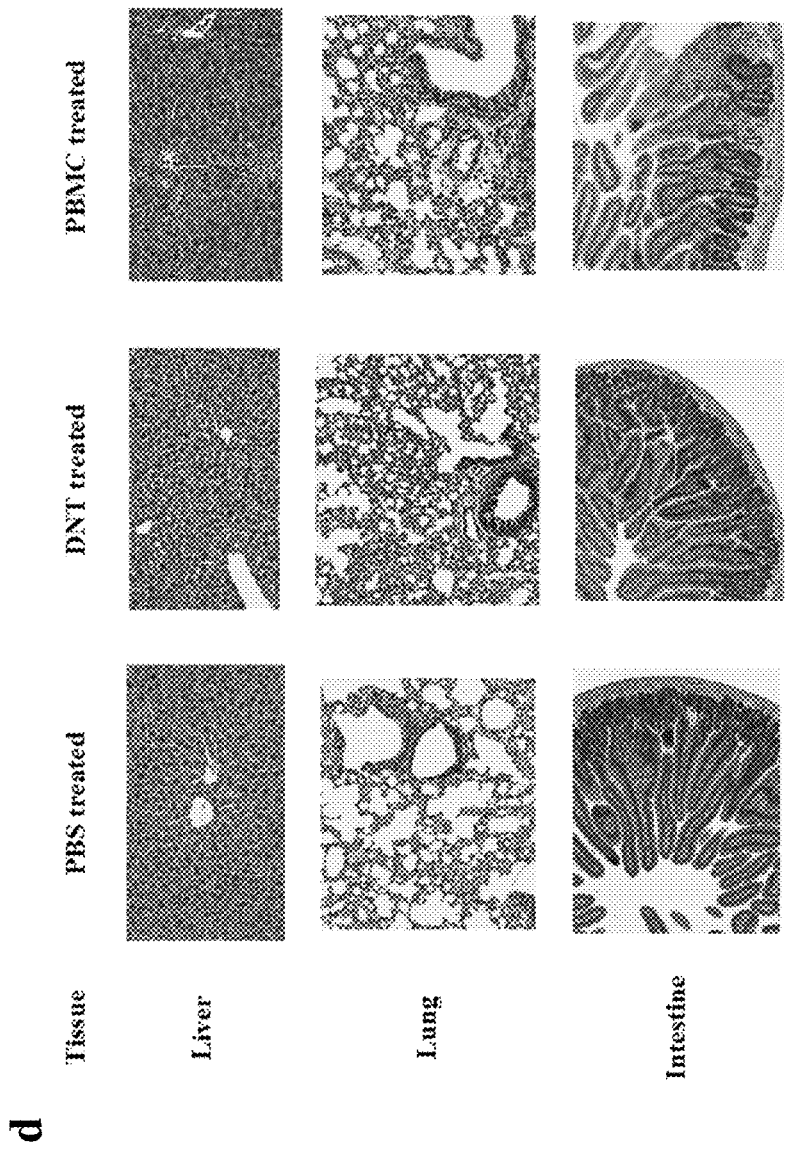
Figure 2E:
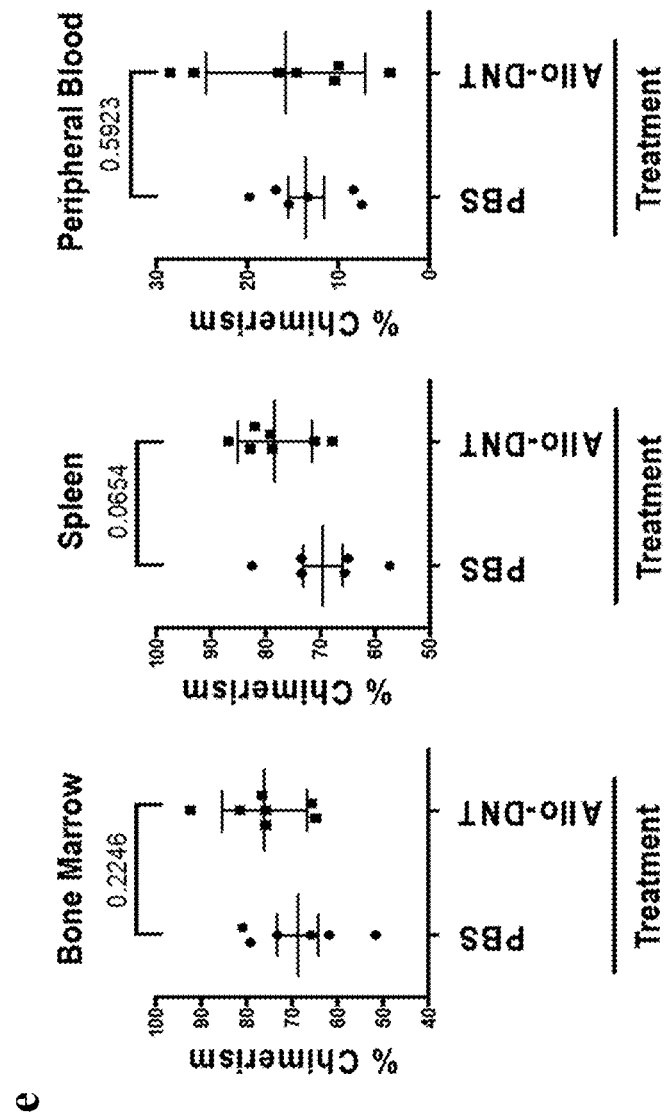
Figure 2:
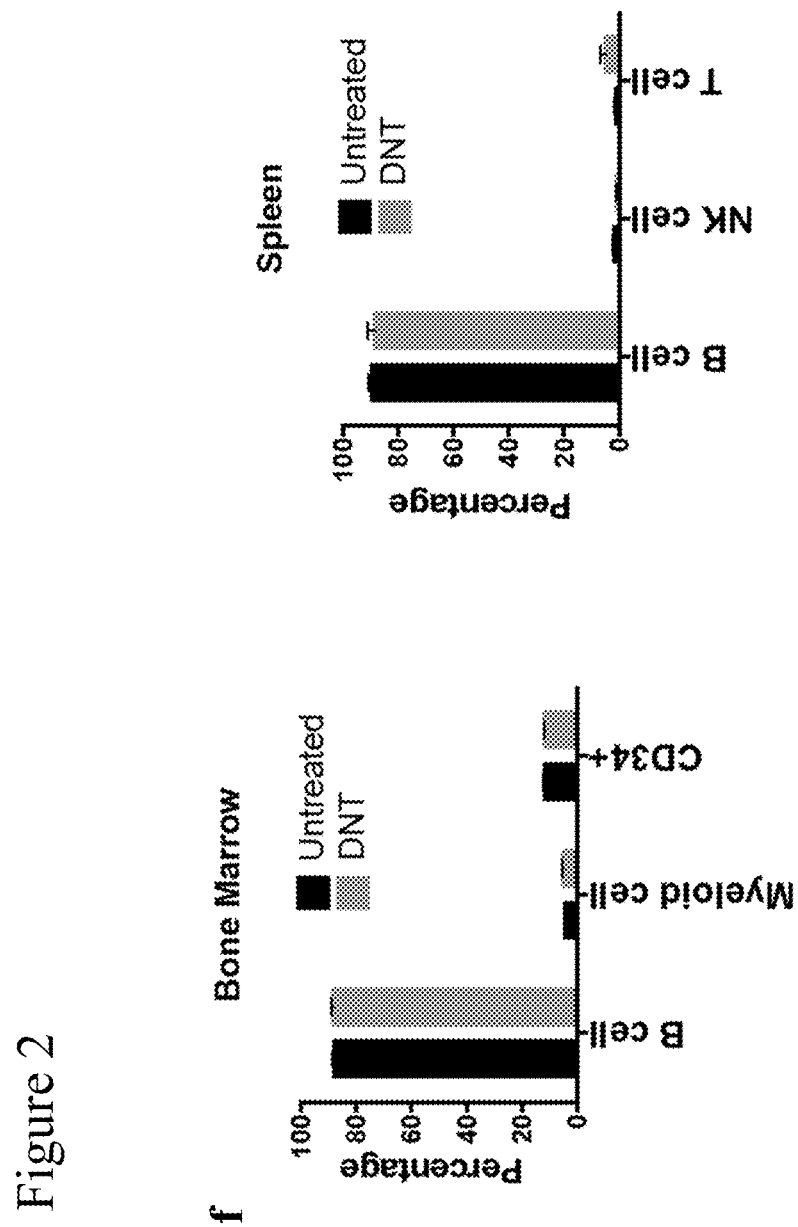

In contrast to autologous HSCT, allogeneic HSCT induces potentially curative graft-versus-leukemia effects[10-14], but is associated with morbidity and mortality due to donor-derived immune cells attacking normal host cells and tissue[14-16]. To determine the potential toxicity of allogeneic DNTs toward normal cells, the cytotoxicity of DNTs expanded from HDs against normal allogeneic PBMCs and Lin$^-$CD34$^+$ hematopoietic stem/progenitor cells (HSPCs) obtained from different HDs was compared to primary AML patient samples and AML cell lines as targets. DNTs displayed potent cytotoxicity against primary AML cell samples (FIG. 1c) and AML cell lines, including a Lin$^-$CD34$^+$ leukemic-stem cell-like cell line KG1a (20 to 40% specific lysis at E:T 8:1) (FIG. 2a), but had virtually no cytotoxicity towards normal allogeneic PBMCs and HSPCs (0-7% specific lysis at E:T 8:1) (FIG. 2a).

To study whether DNTs would have possible toxicity against normal hematopoietic tissues in vivo, ex vivo expanded DNTs or bulk human PBMCs were intravenously infused into NSG mice and monitored for associated morbidities. As expected from prior literatures, PBMCs caused severe xenogeneic GvHD (mediated by CD4 and CD8 T cells)[19-21] as evidenced by weight loss (FIG. 2b) and post-mortem pathology in multiple organs (data not shown). However, when the same numbers of DNTs were infused as PBMC, no signs of GvHD were observed (FIG. 2b). To further assess for potential detrimental effects of allogeneic DNTs on normal HSPCs engraftment and differentiation, NSG mice were transplanted with CD34$^+$CD133$^+$ HD HSPCs and following their engraftment were treated with DNTs from two different HDs (DNTs were allogeneic to the HSPC donor). As observed by others[22,23], we observed consistently high donor chimerism from the HSPC donor (~70-80%) within the spleen and BM, and ~15% in peripheral blood of engrafted mice. No differences were observed in the frequency (FIG. 2c) or differentiation of hematopoietic lineages derived from transplanted HSPC cells (FIG. 2d) between DNT-treated and non-treated mice 8 weeks after DNT-injection. These findings suggest that DNTs do not target allogeneic HSPCs nor their progeny. Furthermore, DNT do not interfere with differentiation of HSPCs into hematopoietic lineages. Together, these results demonstrate that ex vivo expanded allogeneic DNTs have potent anti-leukemia effects but are non-cytotoxic to normal tissues and hematopoietic cells, thus supporting both the efficacy and safety of DNTs as a new therapeutic immunotherapy for patients with myeloid malignancy.

DNTs Produce IFNγ, which Augments its Cytotoxicity Toward AML Cells but not to Normal PBMCs.

Previously, we have shown that ex vivo expanded DNTs express a high level of intracellular IFNγ (Merims et al., 2011). Notably, minimal IFNγ levels were detected in the supernatant from co-cultures of allogeneic DNTs with normal PBMCs (0.50±0.054 ng/ml) and DNT-resistant primary AML cells (0.28±0.10 ng/ml); this corresponded to a low degree of cytotoxicity (FIG. 3b). In contrast, significantly higher levels of IFNγ (3.29±0.58 ng/ml; FIG. 3b) were released within two hours of DNTs co-culture with primary AML cells that were susceptible to DNTs. Indeed, the amount of IFNγ release was correlated with the level of DNT-mediated cytotoxicity toward AML cells (FIG. 3c). Interestingly, addition of IFNγ-neutralizing antibody significantly reduced AML cell death induced by DNTs (FIG. 3d), whereas addition of exogenous recombinant IFNγ (rIFNγ) induced higher level of cytotoxicity (FIG. 3e). However, rIFNγ treatment alone in the absence of DNTs did not change the viability of AML cells, indicating no direct toxicity of IFNγ toward AML cells (FIGS. 3e-i and 3e-ii). Collectively, these data show that IFNγ is indirectly involved in the cytotoxic activity of DNTs against AML.

To further determine whether IFNγ potentiates DNT function and/or sensitizes AML cells, AML cells or DNTs were treated with rIFNγ prior to their co-culture. While pre-treatment of DNT cells with rIFNγ had no significant effect on their function (FIG. 3e-v), rIFNγ pre-treatment of AML cells rendered them more susceptible to cytotoxicity induced by DNTs (18.4% vs. 31.9% for untreated versus rIFNγ pre-treated; FIGS. 3e-iii and 3e-iv). Specific cytolysis was significantly increased in 10 out of 20 primary AML samples after pretreatment with rIFNγ, including 3 out of 6 otherwise DNT-resistant AML samples (FIG. 3f). Interestingly, a greater increase in levels of cytotoxicity was observed when DNT-resistant AML cells were pretreated with rIFNγ than those that were already susceptible to DNTs (increased by 189.1±35.58% vs. 17.33±3.023%, respectively; FIG. 3g). In contrast, pretreating normal allogeneic PBMCs with rIFNγ did not change their susceptibility to DNT-mediated cytotoxicity (FIGS. 3f and 3g). These findings demonstrate that IFNγ released by DNTs can increase the sensitivity of AML cells to DNT-mediated cytotoxicity, supporting the use of rIFNγ as an adjuvant to DNT cell therapy.

DNTs Recognize AML Cells in NKG2D- and DNAM-1-Dependent but TCR-Independent Manner.

To further investigate the mechanisms by which DNTs recognize and target AML cells, we studied the involvement of TCR and screened for expression of known effector-ligand molecules involved in the targeting of cancer cells. The addition of αβ- and γδ-TCR blocking antibodies had no effect on DNT-mediated cytotoxicity of AML cells (FIG. 4a). NKG2D and DNAM-1 are activating receptors known to play a role in anti-cancer immunity[24-30], and are highly expressed on DNTs (FIG. 4b) while their ligands are preferentially expressed on various cancers including AML[28-31]. In contrast these proteins are expressed at low levels on normal PBMCs (FIG. 4c). Blocking either NKG2D, or DNAM-1, or both significantly reduced the ability of DNTs to kill AML cells (FIG. 4d) and the level of IFNγ release (FIG. 4e). These results support a TCR-independent, but NKG2D and DNAM-1 pathways dependent mechanism for DNT-mediated cytotoxicity against AML.

IFNγ Upregulates NKG2D and DNAM-1 Ligands Expression on AML Cells

While IFNγ alone did not induce AML cell death, it increased the susceptibility of AML cells to DNT-mediated cytotoxicity (FIG. 3f). Since both NKG2D and DNAM-1 contributed to DNT-mediated killing of AML cells (FIG. 4d), we hypothesized that IFNγ might increase AML sensitivity by up-regulating NKG2D and DNAM-1 ligand expression. Indeed, treating AML cells with recombinant IFNγ upregulated the expression of NKG2D ligands ULBP1, ULBP2, ULBP3 and MICA/B, as well as DNAM-1 ligands CD112 and CD155 (FIG. 5a) on AML cells but not on normal PBMCs. To further confirm that IFNγ exerted its role through NKG2D and DNAM-1 pathways, AML cells were pre-treated with IFNγ and subsequently used as targets in killing assays in the presence or absence of blocking antibodies to NKG2D and DNAM-1. Pre-incubating AML cells with IFNγ significantly increased their susceptibility to DNT-mediated killing, however, this effect was neutralized by blocking of NKG2D and DNAM-1 (FIG. 5b). Further, the level of cytotoxicity inhibited by NKG2D and DNAM-1 antibodies was significantly greater for IFNγ-pretreated AML targets than untreated ones (22.69%±1.86% vs. 13.65%±0.68%, FIG. 5c). These data indicate that IFNγ increases the sensitivity of leukemic cells, but not normal PBMCs, to DNT-mediated cytotoxicity at least in part by upregulating NKG2D and DNAM-1 ligand expression.

Allogeneic DNTs Effectively Target Chemotherapy Resistant Primary AML Cells In Vitro and In Vivo.

Since chemotherapy resistance is the major cause of low survival rates in AML patients, we next studied the effect of DNTs on chemotherapy resistant AML cells. We found that allogeneic DNT-mediated cytotoxicity in vitro toward primary AML cells from chemotherapy refractory or relapsing patients (FIG. 6a) was comparable to those from chemotherapy-responsive patients (19.30%±3.34% vs. 15.91%±3.63%, FIGS. 6b and 6c). The effect of DNTs against chemotherapy resistant primary AML cells was further validated in vivo using the AML xenograft model as described above (FIG. 1d). AML growth in vivo was significantly reduced in mice that were inoculated with both relapsing (FIG. 6d) and/or chemotherapy refractory (FIG. 6e) AML cells after treatment with a single dose of DNTs.

As DNT treatment did not eliminate all the AML cells (FIGS. 1f, 6d-e), we next studied whether the remaining AML cells were resistant to DNT-mediated cytotoxicity. Residual AML cells were isolated from DNT- and PBS-treated mice, and their susceptibility to DNT-mediated cytotoxicity in vitro was compared with the primary AML cells initially used for the engraftment. AML cells from all three sources displayed similarly, high susceptibility to DNT-mediated cytotoxicity (FIG. 6f), indicating that AML cells did not develop resistance to DNTs after the treatment in vivo. Based on this, we tested the efficacy of multi-dose DNT treatment. A single injection of $2 \times 10^7$ DNTs 3 days after AML inoculation reduced leukemia burden from 30% to 12.8%; this was further reduced to 2.6% with two additional injections of DNTs in 3-day intervals (FIG. 6g). These results suggest that allogeneic DNTs are not only cytotoxic to chemotherapy-resistant primary AML cells, but there is a dose/response relationship suggesting a multi-dosing strategy would be more effective in achieving maximal reduction of leukemic loads as resistance to DNT treatment was not detected.

Here in, we found that allogeneic DNTs from healthy individuals can be efficiently expanded ex vivo, and effectively target a wide spectrum of primary AML samples, including chemotherapy resistant cells. Not only did DNTs elicit effective cytotoxicity in vitro, but they could be transplanted into primary AML xenografts and significantly reduce the leukemic burden without causing toxicity to the host animal. Despite decades of chemotherapy use to treat AML patients, a high relapse-rate remains as a major challenge to patient survival[1-4]. Allo-HSCT can be curative for AML[7,8], but its wide application is limited by toxicity[15,16], restricted applicability in older patients, and donor availability. Other forms of cellular therapies such as CAR-T[32-36] and NK cell therapies[37-39] are currently being studied for AML treatment but have thus far been of limited efficacy in clinic[34,39-42]. Our findings open a new and promising avenue of immunotherapy treatment for leukemia.

The findings that DNTs from a single donor could kill a range of primary AML cells, and AML cells from a single patient showed similar sensitivity to DNTs from different donors point to the broader applicability of allogeneic DNTs as a cellular therapy that is potentially more effective and easier to apply than autologous-based approaches. In particular, an allogeneic approach can provide treatment for AML patients whose own DNTs could not be expanded for autologous therapy.

Mechanistically, we found that DNTs function in a TCR-independent manner at least partially through the innate receptors, NKG2D and DNAM-1. NKG2D and DNAM-1 are activating receptors expressed by NK and subsets of activated T cells; a role for these proteins in cancer immunity has been shown in preclinical studies[24-26,28-30]. AML cells could evade from NKG2D and DNAM-1 mediated NK immunity via shedding of their ligands or down-regulation of the receptors expression[26,30,31], further indicating the importance of these pathways in anti-AML activity. Nevertheless, there are likely other molecules involved in the anti-AML activity of DNTs as the degree of blocking of DNT-mediated cytotoxicity by NKG2D and DNAM-1 blockade was often less than 50% for some targets.

IFNγ is a well-known inflammatory cytokine with a pleotropic function that can elicit both pro- and anti-tumorigenic effects[43-49]. IFNγ mediated anti-leukemia activities include cell cycle-arrest and sensitization of leukemic cells to apoptosis[47-51]. While IFNγ has been shown to down-regulate NKG2D ligand expression on some solid tumors[43,52], we demonstrated that IFNγ induced higher expression of NKG2D and DNAM-1 ligands on AML cells (FIG. 5a), which rendered them more susceptible to DNTs, and theoretically to other cytotoxic cells such as NK cells. Importantly, normal PBMCs express very low levels of NKG2D and DNAM-1 ligands, which are not upregulated by IFNγ. We found that IFNγ does not induce AML cell death directly, which is consistent with the report that clinical trials using IFNγ as a monotherapy did not show noticeable therapeutic efficacy in AML patients[53]. These findings help explain the preferential cytotoxicity of DNTs toward AML cells over normal cells. Further, our data suggest that treatment with IFNγ in combination with DNTs or other cytotoxic cells may achieve greater efficacy against AML.

NKG2D and DNAM-1 ligand expression is regulated by the DNA-damage-repair pathway[54-56], explaining higher levels of ligand expression on transformed cell[28-31,57]. The majority of chemotherapy drugs cause DNA damage and interrupt cell cycle, hence, treatment of myeloma with doxorubicin and bortezomib, has been shown to increase expression of NKG2D and DNAM-1 ligands, and susceptibility towards NK cell-mediated cytotoxicity[56,58]. Similarly, higher levels of NKG2D ligand expression correlated with increased AML susceptibility to NK cells that developed resistance to cytarabine[59,60]. Collectively, these findings support the potential application of DNT therapy as an adjuvant therapy to chemotherapy, which may yield synergistic effects through NKG2D and DNAM-1. Further, as primary AML cells obtained from chemotherapy-resistant and relapsing patients were both are susceptible to DNT-mediated cytotoxicity in vitro and in vivo (FIG. 6), DNTs may be used as a consolidation therapy after conventional chemotherapy to target chemotherapy-resistant minimal residual disease, potentially preventing disease relapse, and to treat chemotherapy refractory leukemias which comprise ~30% of AML cases and for which there are few if any treatment options that might offer long-term survival.

In summary, we demonstrate that allogeneic human DNTs have potent anti-leukemia activity against primary-AML cells, including chemotherapy-resistant cells both in vitro and in vivo in xenograft models, without causing toxicity to normal cells and tissues. Furthermore, we identified molecules critical for DNT-mediated cytotoxicity against AML. Our findings support the use of DNTs expanded from HDs as a new adjuvant cellular immunotherapy to enhance the treatment efficacy and potentially improve survival in patients with AML following conventional chemotherapy.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCE LIST

1. Farag, S. S., et al. Pretreatment cytogenetics add to other prognostic factors predicting complete remission and long-term outcome in patients 60 years of age or older with acute myeloid leukemia: results from Cancer and Leukemia Group B 8461. *Blood* 108, 63-73 (2006).
2. Zahreddine, H. A., et al. The sonic hedgehog factor GLI1 imparts drug resistance through inducible glucuronidation. *Nature* 511, 90-93 (2014).
3. Hoang, V. T., Zepeda-Moreno, A. & Ho, A. D. Identification of leukemia stem cells in acute myeloid leukemia and their clinical relevance. *Biotechnol J* 7, 779-788 (2012).
4. Karp, J. E., et al. Randomized phase II study of two schedules of flavopiridol given as timed sequential therapy with cytosine arabinoside and mitoxantrone for adults with newly diagnosed, poor-risk acute myelogenous leukemia. *Haematologica* 97, 1736-1742 (2012).
5. Majeti, R., et al. CD47 is an adverse prognostic factor and therapeutic antibody target on human acute myeloid leukemia stem cells. *Cell* 138, 286-299 (2009).
6. Hourigan, C. S. & Karp, J. E. Minimal residual disease in acute myeloid leukaemia. *Nat Rev Clin Oncol* 10, 460-471 (2013).
7. Vyas, P., Appelbaum, F. R. & Craddock, C. Reprint of: Allogeneic hematopoietic cell transplantation for acute myeloid leukemia. *Biol Blood Marrow Transplant* 21, S3-10 (2015).
8. Vincent, K., Roy, D. C. & Perreault, C. Next-generation leukemia immunotherapy. *Blood* 118, 2951-2959 (2011).
9. Cornelissen, J. J., et al. The European LeukemiaNet AML Working Party consensus statement on allogeneic HSCT for patients with AML in remission: an integrated-risk adapted approach. *Nat Rev Clin Oncol* 9, 579-590 (2012).
10. Rambaldi, A., Biagi, E., Bonini, C., Biondi, A. & Introna, M. Cell-based strategies to manage leukemia relapse: efficacy and feasibility of immunotherapy approaches. *Leukemia* 29, 1-10 (2015).
11. Campbell, K. S. & Hasegawa, J. Natural killer cell biology: an update and future directions. *The Journal of allergy and clinical immunology* 132, 536-544 (2013).
12. Ruggeri, L., et al. Effectiveness of donor natural killer cell alloreactivity in mismatched hematopoietic transplants. *Science* 295, 2097-2100 (2002).
13. June, C. H., Riddell, S. R. & Schumacher, T. N. Adoptive cellular therapy: a race to the finish line. *Sci Transl Med* 7, 280ps287 (2015).
14. Yanada, M., Matsuo, K., Emi, N. & Naoe, T. Efficacy of allogeneic hematopoietic stem cell transplantation depends on cytogenetic risk for acute myeloid leukemia in first disease remission: a metaanalysis. *Cancer* 103, 1652-1658 (2005).
15. van den Brink, M. R., et al. Relapse after allogeneic hematopoietic cell therapy. *Biol Blood Marrow Transplant* 16, S138-145 (2010).
16. Montero, A., et al. T-cell depleted peripheral blood stem cell allotransplantation with T-cell add-back for patients with hematological malignancies: effect of chronic GVHD on outcome. *Biol Blood Marrow Transplant* 12, 1318-1325 (2006).
17. Merims, S., et al. Anti-leukemia effect of ex vivo expanded DNT cells from AML patients: a potential novel autologous T-cell adoptive immunotherapy. *Leukemia* 25, 1415-1422 (2011).
18. Young, K. J., Kay, L. S., Phillips, M. J. & Zhang, L. Antitumor activity mediated by double-negative T cells. *Cancer Res* 63, 8014-8021 (2003).
19. Covassin, L., et al. Human peripheral blood CD4 T cell-engrafted non-obese diabetic-scid IL2rgamma(null) H2-Ab1 (tm1Gru) Tg (human leucocyte antigen D-related 4) mice: a mouse model of human allogeneic graft-versus-host disease. *Clin Exp Immunol* 166, 269-280 (2011).
20. Fujii, H., et al. Humanized Chronic Graft-versus-Host Disease in NOD-SCID il2rgamma−/− (NSG) Mice with G-CSF-Mobilized Peripheral Blood Mononuclear Cells following Cyclophosphamide and Total Body Irradiation. *PLoS One* 10, e0133216 (2015).
21. van Rijn, R. S., et al. A new xenograft model for graft-versus-host disease by intravenous transfer of human peripheral blood mononuclear cells in RAG2−/− gammac−/− double-mutant mice. *Blood* 102, 2522-2531 (2003).
22. McDermott, S. P., Eppert, K., Lechman, E. R., Doedens, M. & Dick, J. E. Comparison of human cord blood engraftment between immunocompromised mouse strains. *Blood* 116, 193-200 (2010).
23. Drake, A. C., et al. Human CD34+CD133+ hematopoietic stem cells cultured with growth factors including Angptl5 efficiently engraft adult NOD-SCID Il2rgamma−/− (NSG) mice. *PLoS One* 6, e18382 (2011).
24. She, M., et al. Resistance of leukemic stem-like cells in AML cell line KG1a to natural killer cell-mediated cytotoxicity. *Cancer letters* 318, 173-179 (2012).
25. Gertner-Dardenne, J., et al. Human Vgamma9Vdelta2 T cells specifically recognize and kill acute myeloid leukemic blasts. *Journal of immunology* 188, 4701-4708 (2012).
26. Sanchez-Correa, B., et al. Decreased expression of DNAM-1 on NK cells from acute myeloid leukemia patients. *Immunology and cell biology* 90, 109-115 (2012).
27. Karimi, M. A., et al. NKG2D expression by CD8+ T cells contributes to GVHD and GVT effects in a murine model of allogeneic HSCT. *Blood* 125, 3655-3663 (2015).
28. Raulet, D. H. Roles of the NKG2D immunoreceptor and its ligands. *Nature reviews. Immunology* 3, 781-790 (2003).
29. de Andrade, L. F., Smyth, M. J. & Martinet, L. DNAM-1 control of natural killer cells functions through nectin and nectin-like proteins. *Immunology and cell biology* 92, 237-244 (2014).
30. Pende, D., et al. Analysis of the receptor-ligand interactions in the natural killer-mediated lysis of freshly isolated myeloid or lymphoblastic leukemias: evidence for the involvement of the Poliovirus receptor (CD155) and Nectin-2 (CD112). *Blood* 105, 2066-2073 (2005).
31. Zhang, J., Basher, F. & Wu, J. D. NKG2D Ligands in Tumor Immunity: Two Sides of a Coin. *Frontiers in immunology* 6, 97 (2015).
32. Maude, S. L., et al. Chimeric antigen receptor T cells for sustained remissions in leukemia. *The New England journal of medicine* 371, 1507-1517 (2014).
33. Tettamanti, S., Biondi, A., Biagi, E. & Bonnet, D. CD123 AML targeting by chimeric antigen receptors: A novel magic bullet for AML therapeutics? *Oncoimmunology* 3, e28835 (2014).

34. Wang, Q. S., et al. Treatment of CD33-directed chimeric antigen receptor-modified T cells in one patient with relapsed and refractory acute myeloid leukemia. *Mol Ther* 23, 184-191 (2015).
35. Rosenberg, S. A. & Restifo, N. P. Adoptive cell transfer as personalized immunotherapy for human cancer. *Science* 348, 62-68 (2015).
36. Pizzitola, I., et al. Chimeric antigen receptors against CD33/CD123 antigens efficiently target primary acute myeloid leukemia cells in vivo. *Leukemia* 28, 1596-1605 (2014).
37. Miller, J. S., et al. Successful adoptive transfer and in vivo expansion of human haploidentical NK cells in patients with cancer. *Blood* 105, 3051-3057 (2005).
38. Bachanova, V., et al. Clearance of acute myeloid leukemia by haploidentical natural killer cells is improved using IL-2 diphtheria toxin fusion protein. *Blood* 123, 3855-3863 (2014).
39. Curti, A., et al. Successful transfer of alloreactive haploidentical KIR ligand-mismatched natural killer cells after infusion in elderly high risk acute myeloid leukemia patients. *Blood* 118, 3273-3279 (2011).
40. Arpinati, M. & Curti, A. Immunotherapy in acute myeloid leukemia. *Immunotherapy* 6, 95-106 (2014).
41. Rooney, C. M. Can Treg elimination enhance NK cell therapy for AML? *Blood* 123, 3848-3849 (2014).
42. Ritchie, D. S., et al. Persistence and efficacy of second generation CAR T cell against the LeY antigen in acute myeloid leukemia. *Mol Ther* 21, 2122-2129 (2013).
43. Bui, J. D., Carayannopoulos, L. N., Lanier, L. L., Yokoyama, W. M. & Schreiber, R. D. IFN-dependent down-regulation of the NKG2D ligand H60 on tumors. *Journal of immunology* 176, 905-913 (2006).
44. Shankaran, V., et al. IFNgamma and lymphocytes prevent primary tumour development and shape tumour immunogenicity. *Nature* 410, 1107-1111 (2001).
45. Beatty, G. L. & Paterson, Y. IFN-Can Promote Tumor Evasion of the Immune System In Vivo by Down-Regulating Cellular Levels of an Endogenous Tumor Antigen. *The Journal of Immunology* 165, 5502-5508 (2000).
46. Morel, S., et al. Processing of Some Antigens by the Standard Proteasome but Not by the Immunoproteasome Results in Poor Presentation by Dendritic Cells. *Immunity* 12, 107-117 (2000).
47. Acquavella, N., et al. Type I cytokines synergize with oncogene inhibition to induce tumor growth arrest. *Cancer Immunol Res* 3, 37-47 (2015).
48. Matsushita, H., et al. Cytotoxic T lymphocytes block tumor growth both by lytic activity and IFNgamma-dependent cell-cycle arrest. *Cancer Immunol Res* 3, 26-36 (2015).
49. Zaidi, M. R. & Merlino, G. The two faces of interferon-gamma in cancer. *Clinical cancer research: an official journal of the American Association for Cancer Research* 17, 6118-6124 (2011).
50. Ersvaer, E., Skavland, J., Ulvestad, E., Gjertsen, B. T. & Bruserud, O. Effects of interferon gamma on native human acute myelogenous leukaemia cells. *Cancer immunology, immunotherapy: CII* 56, 13-24 (2007).
51. Varela, N., et al. Interferon-gamma sensitizes human myeloid leukemia cells to death receptor-mediated apoptosis by a pleiotropic mechanism. *The Journal of biological chemistry* 276, 17779-17787 (2001).
52. Schwinn, N., et al. Interferon-gamma down-regulates NKG2D ligand expression and impairs the NKG2D-mediated cytolysis of MHC class I-deficient melanoma by natural killer cells. *International journal of cancer. Journal international du cancer* 124, 1594-1604 (2009).
53. Stone, R. M., et al. Recombinant human gamma interferon administered by continuous intravenous infusion in acute myelogenous leukemia and myelodysplastic syndromes. *American journal of clinical oncology* 16, 159-163 (1993).
54. Cerboni, C., et al. The DNA Damage Response: A Common Pathway in the Regulation of NKG2D and DNAM-1 Ligand Expression in Normal, Infected, and Cancer Cells. *Frontiers in immunology* 4, 508 (2014).
55. Gasser, S., Orsulic, S., Brown, E. J. & Raulet, D. H. The DNA damage pathway regulates innate immune system ligands of the NKG2D receptor. *Nature* 436, 1186-1190 (2005).
56. Fine, J. H., et al. Chemotherapy-induced genotoxic stress promotes sensitivity to natural killer cell cytotoxicity by enabling missing-self recognition. *Cancer Res* 70, 7102-7113 (2010).
57. Verheyden, S. & Demanet, C. NK cell receptors and their ligands in leukemia. *Leukemia* 22, 249-257 (2008).
58. Soriani, A., et al. ATM-ATR-dependent up-regulation of DNAM-1 and NKG2D ligands on multiple myeloma cells by therapeutic agents results in enhanced NK-cell susceptibility and is associated with a senescent phenotype. *Blood* 113, 3503-3511 (2009).
59. Ogbomo, H., Michaelis, M., Klassert, D., Doerr, H. W. & Cinatl, J., Jr. Resistance to cytarabine induces the up-regulation of NKG2D ligands and enhances natural killer cell lysis of leukemic cells. *Neoplasia* 10, 1402-1410 (2008).
60. Nanbakhsh, A., et al. c-Myc regulates expression of NKG2D ligands ULBP1/2/3 in AML and modulates their susceptibility to NK-mediated lysis. *Blood* 123, 3585-3595 (2014).

The invention claimed is:

1. A method of treating leukemia or lymphoma in a subject in need thereof, comprising administering to the subject an effective amount of double negative T cells (DNTs) and Interferon-γ.

2. The method of claim 1, wherein the double negative T cells (DNTs) are administered either prior to, simultaneously, or subsequent to the administration of Interferon-γ.

3. The method of claim 1, wherein the DNTs are CD4−CD8−, preferably expressing CD3−TCR complex; and further preferably have the phenotype CD3+, γδ-TCR+or αβ-TcR+, CD4−, CD8−, α-GalCer-loaded-CD1d−, PD-1−, CTLA4−; CD3+, γδ-TCR+or αβ-TcR+, CD4−, CD8−, α-GalCer-loaded-CD1d, PD-1−, CTLA4−, CD44+, CD28−; CD3+, CD4−, CD8−, α-Gal−, PD-1−, CTLA4−, CD44+; or CD3+, CD4−, CD8−, α-GalCer-loaded-CD1d−, Jα24-Vα14 TCR−, CD44+, PD-1−, CTLA4−, CD45RO+.

4. The method of claim 1, wherein the majority of DNTs are those which are CD4−CD8−, and are γδ-TCR+.

5. The method of claim 1, wherein the majority of DNTs are those which are CD4−CD8−, and are αβ-TcR+.

6. The method of claim 1, wherein the leukemia is acute myeloid leukemia (AML).

7. The method of claim 1, wherein the DNTs are autologous.

8. The method of claim 7, wherein the subject from which the autologous DNT's are obtained has one or more detectable cancer cells.

9. The method of claim 7, wherein the subject from which the DNTs are obtained has previously been treated for cancer.

10. The method of claim 5, wherein the subject from which the DNTs are obtained is not in complete remission.

11. The method of claim 7, wherein the DNTs are obtained from the subject prior to, during or after chemotherapy.

12. The method of claim 11, wherein the DNTs are obtained from the subject after one or more rounds of chemotherapy.

13. The method of claim 1, wherein the DNTs are allogeneic.

14. The method of claim 13, wherein the DNTs are from one or more individuals without cancer.

15. The method of claim 1, wherein the DNTs are obtained from a sample comprising peripheral blood mononuclear cells (PBMC).

16. The method of claim 15, wherein the sample is a blood sample.

17. The method of claim 1, wherein the DNTs have been expanded in vitro or ex vivo.

18. The method of claim 1, wherein the subject has recurrent, relapsing or refractory AML.

19. The method of claim 18, wherein the recurrent or relapsing AML is caused by minimal residual disease (MRD) or leukemic stem cells.

20. The method of claim 1, wherein the DNTs are administered to the subject by intravenous injection.

21. The method of claim 1, wherein the DNTs are administered to the subject prior to, during or after chemotherapy.

22. The method of claim 21, wherein the DNTs are administered to the subject the same day, within 3 days, within 1 week, within 2 weeks, within 3 weeks or within 1 month of chemotherapy.

23. The method of claim 1, further comprising administering to the subject one or more additional doses of an effective amount of DNTs.

24. The method of claim 23, wherein the additional doses are administered at least 3 days after the last dose of DNTs, at least 5 days after the last dose of DNTs, or optionally between 3 days and two weeks after the last dose of DNTs.

25. A method of treating leukemia or lymphoma in a subject in need thereof, comprising administering to the subject an effective amount of double negative T cells (DNTs), wherein the subject has previously been administered Interferon-γ.

* * * * *